(12) United States Patent
Alli et al.

(10) Patent No.: US 11,795,252 B2
(45) Date of Patent: *Oct. 24, 2023

(54) COMPOSITIONS WITH HIGH REFRACTIVE INDEX AND ABBE NUMBER

(71) Applicant: JOHNSON & JOHNSON SURGICAL VISION, INC., Irvine, CA (US)

(72) Inventors: Azaam Alli, Jacksonville, FL (US); Stephen Arnold, Jacksonville, FL (US); Scott L. Joslin, Ponte Vedra Beach, FL (US); Bart A. Johnson, Laguna Beach, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/451,125

(22) Filed: Oct. 15, 2021

(65) Prior Publication Data

US 2022/0135720 A1 May 5, 2022

Related U.S. Application Data

(60) Provisional application No. 63/107,356, filed on Oct. 29, 2020.

(51) Int. Cl.
| | | |
|---|---|---|
| *C08F 220/40* | (2006.01) | |
| *C08F 220/28* | (2006.01) | |
| *A61L 27/16* | (2006.01) | |
| *A61L 27/50* | (2006.01) | |
| *C08L 33/14* | (2006.01) | |
| *G02B 1/04* | (2006.01) | |

(52) U.S. Cl.
CPC .......... *C08F 220/281* (2020.02); *A61L 27/16* (2013.01); *A61L 27/50* (2013.01); *C08L 33/14* (2013.01); *A61L 2430/16* (2013.01); *C08F 2800/20* (2013.01); *C08F 2810/20* (2013.01); *G02B 1/043* (2013.01)

(58) Field of Classification Search
CPC ............... C08F 220/281; C08F 220/40; C08F 2800/20; C08F 2810/20; C08F 220/68; C08F 222/102; A61L 27/52; A61L 2430/16; A61L 27/16; A61L 27/50; G02B 1/043; C08L 33/14
See application file for complete search history.

(56) References Cited

U.S. PATENT DOCUMENTS

| | | |
|---|---|---|
| 4,131,729 A | 12/1978 | Schmitt et al. |
| 4,573,998 A | 3/1986 | Mazzocco |
| 4,731,079 A | 3/1988 | Stoy |
| 5,233,007 A | 8/1993 | Yang |
| 5,290,892 A | 3/1994 | Namdaran et al. |
| 5,357,024 A | 10/1994 | Leclaire |
| 5,403,901 A | 4/1995 | Namdaran et al. |
| 5,424,339 A | 6/1995 | Zanka et al. |
| 5,433,746 A | 7/1995 | Namdaran et al. |
| 5,541,278 A | 7/1996 | Raleigh et al. |
| 5,648,402 A | 7/1997 | Nunez et al. |
| 5,674,960 A | 10/1997 | Namdaran et al. |
| 5,693,095 A | 12/1997 | Freeman et al. |
| 5,694,195 A | 12/1997 | Engardio et al. |
| 5,861,031 A | 1/1999 | Namdaran et al. |
| 5,910,537 A | 6/1999 | Feingold et al. |
| 5,913,898 A | 6/1999 | Feingold |
| 6,140,438 A | 10/2000 | Ojio et al. |
| 6,313,187 B2 | 11/2001 | LeBoeuf et al. |
| 6,313,251 B1 | 11/2001 | Toh et al. |
| 6,353,069 B1 | 3/2002 | Freeman et al. |
| 6,367,929 B1 | 4/2002 | Maiden et al. |
| 6,416,550 B2 | 7/2002 | Freeman |
| 6,491,721 B2 | 12/2002 | Freeman et al. |
| 6,699,953 B2 | 3/2004 | Oshikiri et al. |
| 6,770,735 B2 | 8/2004 | Tanaka et al. |
| 6,852,793 B2 | 2/2005 | Salamone et al. |
| 7,009,024 B2 | 3/2006 | Salamone et al. |
| 7,169,874 B2 | 1/2007 | Salamone et al. |
| 7,217,778 B2 | 5/2007 | Verbruggen |
| 7,279,538 B2 | 10/2007 | Lai et al. |
| 7,295,749 B2 | 11/2007 | Kitamura et al. |
| 7,297,160 B2 | 11/2007 | Salamone et al. |
| 7,301,705 B2 | 11/2007 | Yoshimura et al. |
| 7,423,108 B2 | 9/2008 | Kunzler et al. |
| 7,632,904 B2 | 12/2009 | Salamone et al. |
| 7,714,090 B2 | 5/2010 | Iwamoto et al. |
| 7,763,682 B2 | 7/2010 | Lowery et al. |
| 7,767,779 B2 | 8/2010 | Jallouli et al. |
| 7,928,171 B2 | 4/2011 | Makker et al. |

(Continued)

FOREIGN PATENT DOCUMENTS

| | | |
|---|---|---|
| AU | 734097 B2 | 6/2001 |
| CA | 2059328 A1 | 10/1992 |

(Continued)

OTHER PUBLICATIONS

Translation of JPH05-202346 (Year: 1993).*
Translation of JPH0726193 (Year: 1995).*

*Primary Examiner* — Robert C Boyle

(74) *Attorney, Agent, or Firm* — Johnson & Johnson Surgical Vision, Inc.

(57) ABSTRACT

Disclosed are co-polymers which are produced from reactive monomer mixtures and which have both high refractive index and a high Abbe number. These materials are well suited for use as implantable ophthalmic devices and have a refractive index which may be edited through application of energy. When used for an intraocular lens, the high refractive index allows for a thin lens which compresses to allow a small incision size.

25 Claims, No Drawings

(56) References Cited

U.S. PATENT DOCUMENTS

| | | |
|---|---|---|
| 8,148,445 B1 | 4/2012 | Laredo |
| 8,293,858 B1 | 10/2012 | Laredo |
| 8,323,799 B2 | 12/2012 | Hu et al. |
| 8,329,763 B2 | 12/2012 | Werner |
| 8,449,610 B2 | 5/2013 | Laredo et al. |
| 8,470,948 B2 | 6/2013 | Stiegman |
| 8,681,428 B1 | 3/2014 | Brown |
| 8,759,414 B2 | 6/2014 | Muller-Lierheim et al. |
| 9,012,566 B2 | 4/2015 | Buhler et al. |
| 9,289,531 B2 | 3/2016 | Jiang et al. |
| 9,427,493 B2 | 8/2016 | Kahook et al. |
| 9,475,967 B2 | 10/2016 | Lipscomb et al. |
| 9,622,853 B2 | 4/2017 | Argal |
| 9,820,850 B2 | 11/2017 | Mentak |
| 9,864,102 B2 | 1/2018 | Laredo et al. |
| 9,921,341 B2 | 3/2018 | Laredo et al. |
| 10,053,249 B2 | 8/2018 | Stutz et al. |
| 10,117,965 B1 | 11/2018 | Suganuma et al. |
| 10,155,349 B2 | 12/2018 | Pruitt et al. |
| 10,408,947 B2 | 9/2019 | Beacham et al. |
| 10,408,974 B2 | 9/2019 | Schlueter |
| 10,626,206 B2 | 4/2020 | Terrisse |
| 10,722,612 B2 | 7/2020 | Jiang et al. |
| 2002/0049290 A1 | 4/2002 | Vanderbilt |
| 2004/0248038 A1 | 12/2004 | Yokoyama et al. |
| 2005/0254003 A1 | 11/2005 | Jani et al. |
| 2007/0004863 A1 | 1/2007 | Mentak |
| 2007/0222095 A1 | 9/2007 | Zanini et al. |
| 2007/0249794 A1 | 10/2007 | Evans et al. |
| 2008/0200582 A1 | 8/2008 | Craciun et al. |
| 2011/0177256 A1 | 7/2011 | McAneney et al. |
| 2012/0202916 A1 | 8/2012 | Laredo et al. |
| 2012/0309919 A1 | 12/2012 | Laredo |
| 2013/0253159 A1 | 9/2013 | Benz et al. |
| 2013/0345364 A1 | 12/2013 | Alli et al. |
| 2014/0163130 A1 | 6/2014 | Zhang et al. |
| 2015/0299500 A1 | 10/2015 | Haraguchi et al. |
| 2015/0321991 A1 | 11/2015 | Ponrathnam et al. |
| 2016/0235886 A1 | 8/2016 | Jiang et al. |
| 2017/0072601 A1 | 3/2017 | Akasaki |
| 2018/0009922 A1 | 1/2018 | Alli et al. |
| 2018/0011222 A1 | 1/2018 | Alli et al. |
| 2018/0011223 A1 | 1/2018 | Alli et al. |
| 2018/0319901 A1 | 11/2018 | Hampson et al. |
| 2019/0000364 A1* | 1/2019 | Balaconis ............ A61B 5/1459 |
| 2019/0225726 A1 | 7/2019 | DeSousa et al. |
| 2019/0314547 A1 | 10/2019 | Sui et al. |
| 2019/0338092 A1 | 11/2019 | Reit et al. |
| 2019/0339419 A1 | 11/2019 | Schlueter |
| 2020/0038548 A1 | 2/2020 | Suganuma et al. |
| 2020/0038549 A1 | 2/2020 | Stoy et al. |
| 2020/0123410 A1 | 4/2020 | Reit et al. |
| 2020/0165411 A1 | 5/2020 | Takagi et al. |
| 2020/0255709 A1 | 8/2020 | Reit et al. |
| 2020/0347166 A1 | 11/2020 | Azaam et al. |
| 2020/0347167 A1 | 11/2020 | Azaam et al. |

FOREIGN PATENT DOCUMENTS

| | | |
|---|---|---|
| CA | 2752046 A1 | 8/2010 |
| CA | 2802793 A1 | 2/2012 |
| CN | 102822217 A | 12/2012 |
| CN | 102140149 B | 3/2013 |
| CN | 109337591 A | 2/2019 |
| CN | 105985749 B | 6/2019 |
| CN | 105985750 B | 6/2019 |
| CN | 106459316 B | 3/2020 |
| CN | 111512227 A | 8/2020 |
| CN | 107429129 B | 9/2020 |
| CN | 109438614 B | 1/2021 |
| DE | 4010784 C2 | 11/1994 |
| EP | 1003795 B1 | 2/2004 |
| EP | 2906970 B1 | 11/2016 |
| EP | 3627212 A1 | 3/2020 |
| FR | 2774998 A1 | 8/1999 |
| JP | H05-202346 * | 8/1993 |
| JP | H05202346 A | 8/1993 |
| JP | H0726193 * | 1/1995 |
| JP | 2004075879 A | 3/2004 |
| JP | 2006328094 A | 12/2006 |
| JP | 2007016141 A | 1/2007 |
| JP | 2007077215 A | 3/2007 |
| JP | 2007091921 A | 4/2007 |
| JP | 2007169560 A | 7/2007 |
| JP | 2007186630 A | 7/2007 |
| JP | 2007262175 A | 10/2007 |
| JP | 2009227778 A | 10/2009 |
| JP | 2009256275 A | 11/2009 |
| JP | 2009256662 A | 11/2009 |
| JP | 2011038050 A | 2/2011 |
| JP | 2012052098 A | 3/2012 |
| JP | 2012082386 A | 4/2012 |
| JP | 2013010842 A | 1/2013 |
| JP | 2013234127 A | 11/2013 |
| KR | 20080023016 A | 3/2008 |
| KR | 20110109938 A | 10/2011 |
| WO | 9727223 A1 | 7/1997 |
| WO | 0011097 A1 | 3/2000 |
| WO | 0064956 A1 | 11/2000 |
| WO | 2006043409 A1 | 4/2006 |
| WO | 2011125956 A1 | 10/2011 |
| WO | 2012004744 A2 | 1/2012 |
| WO | 2012167124 A1 | 12/2012 |
| WO | 2013048993 A1 | 4/2013 |
| WO | 2014054698 A1 | 4/2014 |
| WO | 2015016363 A1 | 2/2015 |
| WO | 2015068839 A1 | 5/2015 |
| WO | 2015132605 A1 | 9/2015 |
| WO | 2015170278 A1 | 11/2015 |
| WO | 2017072186 A1 | 5/2017 |
| WO | 2018212063 A1 | 11/2018 |
| WO | 2018229653 A1 | 12/2018 |

* cited by examiner

COMPOSITIONS WITH HIGH REFRACTIVE INDEX AND ABBE NUMBER

CROSS-REFERENCE TO RELATED APPLICATIONS

This application claims the benefit under 35 U.S.C. § 119(e) of U.S. Provisional Patent Application No. 63/107,356, filed Oct. 29, 2020, which is incorporated herein by reference in its entirety.

FIELD OF THE DISCLOSURE

This disclosure is directed to co-polymers produced from reactive monomer mixtures which, when polymerized, form acrylic materials having high refractive indexes and high Abbe numbers. These materials, which may have an editable refractive index, are designed for use in ophthalmic devices, such as intraocular implants or lenses.

BACKGROUND OF THE DISCLOSURE

Cataract surgery is commonly performed to replace the natural eye lens that has become opaque. Materials that are used to replace the natural crystalline lens must be soft and have excellent flexibility so that, once formed into a lens, they may be folded and passed through an incision which is typically about 2 mm. Furthermore, the material must have excellent transparency and little to no glistening. Having a high refractive index allows for a thinner lens to be used. A material with a high Abbe number demonstrates less dispersion. This, in turn, allows for improved optical results and less light scattering. Combining a high refractive index with a high Abbe number provides preferable optical characteristics for a material.

One of the first patents in this area, U.S. Pat. No. 4,573,998, to Mazzocco, discloses a deformable intraocular lens that can be rolled to fit through a relatively small incision. The deformable lens is inserted into the eye while it is held in its rolled configuration, then released inside the chamber of the eye. The elastic properties of the lens cause it to resume its molded shape after insertion into the eye. Mazzocco discloses polyurethane elastomers, silicone elastomers, hydrogel polymer compounds, organic or synthetic gel compounds and combinations thereof as suitable materials for the deformable lens.

Friction from inside the delivery device and physician force during delivery can damage the lens. To overcome this issue, some delivery devices are coated to provide extra lubricity. For example, U.S. Pat. No. 8,323,799, to Hu, discloses a soft, flexible highly lubricious coatings for polymeric IOL insertion cartridges that allow IOLs to be easily inserted through small bore cartridges suitable for use with small (less than 3 mm) incisions. While such coatings are helpful, there is a need to further reduce friction forces imposed on the lens during insertion.

Accordingly, there is a need for a material, with a relatively high refractive index and Abbe number, which can be used to form a flexible intraocular lens which can be simply rolled or folded into a configuration which will fit through a small incision. There is further need for such a material to have internal lubricity.

SUMMARY OF THE DISCLOSURE

In certain embodiments, the present disclosure relates a composition made by free radical polymerization of a reactive monomer mixture comprising:

a. at least one low glass transition temperature monomer;
b. a tricyclo[5.2.1.0$^{2,6}$]decanedimethanol di(meth)acrylate cross-linking agent; and
c. an ethylene glycol dicyclopentenyl ether (meth)acrylate;
  wherein the concentration of the ethylene glycol dicyclopentenyl ether (meth)acrylate in the reactive monomer mixture excluding any diluent is greater than 80 weight percent; and
  wherein the composition exhibits a refractive index of at least 1.45 and an Abbe number of at least 39 ("Composition (A)").

In certain embodiments, the present disclosure provides a device comprising Composition (A). In certain other embodiments, the device is an ophthalmic device. In particular embodiments, the ophthalmic device comprises a lens, inlay, outlay, or insert selected from an intraocular implant or lens, a contact lens, a corneal inlay, a corneal outlay, and a corneal insert. In specific embodiments, the ophthalmic device is an intraocular implant or lens. More specifically, the present disclosure also provides intraocular implants and/or lenses made of at least partially or completely from Composition (A).

In still yet other embodiments, the present disclosure provides a method for making an ophthalmic device, the method comprising the steps of: (a) providing Composition (A) and (b) forming an ophthalmic device from any of said compositions. In other embodiments, the presently disclosed subject matter provides a method for making an ophthalmic device, the method comprising: (a) preparing a blank from Composition (A) and (b) machining an ophthalmic device from the blank. In other embodiments, the presently disclosed subject matter provides a method for making an ophthalmic device, the method comprising molding an ophthalmic device from Composition (A).

In still other embodiments, the presently disclosed subject matter provides a method for making an ophthalmic device, the method comprising (a) molding an ophthalmic device from Composition (A) and (b) refining the molded lens surface via machining.

In certain embodiments of any of the above methods, the method further comprises the step of extracting the ophthalmic device with a solvent. In certain embodiments, the method further comprises the step of hydrating the extracted ophthalmic device with at least one aqueous solution. In particular embodiments, the method further comprises an irradiation step using a laser. In more particular embodiments, the method further comprises a step of sterilizing the ophthalmic device.

DETAILED DESCRIPTION OF THE DISCLOSURE

It is to be understood that the disclosure is not limited to the details of construction or process steps set forth in the following description. The disclosure is capable of other embodiments and of being practiced or being carried out in various ways using the teaching herein.

A. Definitions

With respect to the terms used in this disclosure, the following definitions are provided.

Unless defined otherwise, all technical and scientific terms used herein have the same meaning as commonly understood by one of ordinary skill in the art to which the disclosure belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

The term "reactive monomer mixture" refers to a mixture of components (both reactive and non-reactive) which are mixed together and when subjected to polymerization conditions, form the presently disclosed compositions and ophthalmic devices. The reactive mixture may include reactive components such as monomers, macromers, prepolymers, cross-linkers, initiators, diluents, and additional components, including, but not limited to, wetting agents, release agents, dyes, light absorbing compounds, such as ultraviolet-high energy visible light (UV/HEV) absorbers, pigments, dyes and photochromic compounds, any of which may be reactive or non-reactive but are capable of being retained within the resulting biomedical device, e.g., an ophthalmic device, as well as active components, including pharmaceutical and nutraceutical compounds, and any diluents. It will be appreciated that a wide range of additives may be added based upon the biomedical device which is made, and its intended use. In some embodiments, concentrations of components of the reactive mixture are given in weight % of all components in the reaction mixture, excluding diluent. When diluents are used their concentrations are given as weight % based upon the amount of all components in the reaction mixture and the diluent.

"Reactive components" are the components in the reactive monomer mixture which become part of the structure of the polymeric network of the resulting composition, by covalent bonding or hydrogen bonding. Diluents and processing aids which do not become part of the structure of the polymer are not reactive components.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula $[***]_n$, is used to depict the number of repeating units in a polymer's chemical formula, the formula should be interpreted to represent the number average molecular weight of the macromolecule.

The term "individual" includes humans and non-human vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular implants, intraocular lenses, and contact lenses. The biomedical devices may be ophthalmic devices, particularly ophthalmic implants or ophthalmic lenses made from the reactive monomer compositions described herein.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise an intraocular implant, intraocular lens, or contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet (UV) light absorbing, visible (VIS) light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

"Intraocular lens" refers to a lens implanted in an eye. In some embodiments, the intraocular lens is implanted in the eye to replace an existing crystalline lens (such as, for example, because the existing lens has been clouded over by a cataract, or as a form of refractive surgery to change the eye's optical power).

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or ionic polymerization (e.g., cationic polymerization), for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyllactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500 Daltons and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and cross-linkers may be used interchangeably.

A "low glass transition temperature monomer" is a monomer that, when incorporated into a polymer with one or more other monomers and cross-linkers, reduces the glass transition temperature of the resulting polymer compared to a polymer that does not include the low glass transition temperature monomer. In certain embodiments, a "low glass transition temperature monomer" is a monomer whose homopolymer exhibits a glass transition temperature during a second heating scan that is lower than 0° C., lower than minus 5° C. (−5° C.), lower than minus 10° C. (−10° C.), lower than minus 15° C. (−15° C.), or lower than minus 20° C. (−20° C.). Test samples of such homopolymers can be analyzed (in duplicate) on a DSC Q2000 TA instrument or similar instrument at heating rates of 10° C./minute and cooling rates of 5° C./minute under a nitrogen gas atmosphere. Low glass transition temperature monomers can be hydrophilic or hydrophobic.

A "polymer" is a target macromolecule composed of the repeating units of the monomers used during polymerization. A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer. The terms "reactive mixture" and "reactive monomer mixture" refer to the mixture of components (both retained and non-retained) which are mixed together and, when subjected to polymerization conditions, result in formation of a polymeric network as well as biomedical devices, ophthalmic devices, intraocular implants, contact lenses, and intraocular lenses made therefrom. The reactive mixture may comprise retained components such as monomers, macromers, prepolymers, cross-linkers, and initiators, additives such as wetting agents, polymers, dyes, light absorbing compounds such as UV/HEV absorbers, pigments, photochromic compounds, pharmaceutical compounds, and/or nutraceutical compounds, any of which may be reactive or non-reactive but are capable of being retained within the resulting biomedical device. The reactive mixture may also contain non-retained components which are intended to be removed from the device prior to its use, such as diluents. It will be appreciated that a wide range of additives may be added based upon the biomedical device which is made and its intended use. Concentrations of components of the reactive mixture are expressed as weight percentages of all retained components in the reactive mixture, therefore excluding non-retained components such as diluent. When diluents are used, their concentrations are expressed as weight percentages based upon the amount of all components in the reactive mixture (including the diluent).

"Retained components" are the polymerizable compounds (such as monomers, macromers, oligomers, prepolymers, and cross-linkers) in the reactive mixture, as well as any other components in the reactive mixture which are intended to substantially remain in the polymeric network after polymerization and all work-up steps (such as extraction steps) and packaging steps have been completed. Retained components may be retained in the polymeric network by covalent bonding, hydrogen bonding, electrostatic interactions, the formation of interpenetrating polymeric networks, or any other means. Components that are intended to release from the biomedical device once it is in use are still considered "retained components." For example, pharmaceutical or nutraceutical components in a contact lens which are intended to be released during wear are considered "retained components." Components that are intended to be removed from the polymeric network during the manufacturing process (e.g., by extraction), such as diluents, are "non-retained components."

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" or "aliphatic" are used interchangeably herein and refer to an optionally substituted linear or branched alkyl group containing the indicated number of carbon atoms. If no number is indicated, then alkyl (including any optional substituents on alkyl) may contain any of 1 to 16 carbon atoms, including 1, 2, 3, 4, 5, 6, 7, 8, 9, 10, 11, 12, 13, 14, 15, and 16 carbon atoms. Preferably, the alkyl group contains 1 to 10 carbon atoms, including 1, 2, 3, 4, 5, 6, 7, 8, 9, and 10 carbon atoms, alternatively 1 to 8 carbon atoms, including 1, 2, 3, 4, 5, 6, 7, and 8 carbon atoms, alternatively 1 to 6 carbon atoms, including 1, 2, 3, and 4 carbon atoms, or alternatively 1 to 4 carbon atoms, including 1, 2, 3, and 4. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as —$CH_2$—, —$CH_2CH_2$—, —$CH_2CH_2CH_2$—, —$CH_2CH(CH_3)CH_2$—, and —$CH_2CH_2CH_2CH_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, 1-4 carbons, or 1-2 carbons. "Haloalkyl" includes perhaloalkyl groups, in which each hydrogen atom of the alkyl group is replaced with a halogen atom, such as —$CF_3$— or —$CF_2CF_3$—. "Haloalkylene" means a divalent haloalkyl group, such as —$CH_2CF_2$—.

"Hydroxy" refers to an —OH group.

"Hydroxyalkyl" refers to an alkyl group, as defined herein, substituted with at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

"Cycloalkyl" or "cycloaliphatic" are used interchangeably herein and refer to an optionally substituted cyclic hydrocarbon containing the indicated number of ring carbon atoms. If no number is indicated, then cycloalkyl may contain 3 to 20 ring carbon atoms (e.g., 3 to 12 ring carbon atoms). Cycloaliphatic groups can be monocyclic, bicyclic, tricyclic, bridged, fused, and/or spirocyclic. Cycloaliphatic groups can also have one or more double bonds, provided that the group is not fully aromatic. Preferred monocyclic cycloaliphatic groups are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Arylalkyl" refers to an aryl group, as defined herein, appended to the parent molecular moiety through an alkyl group, as defined herein. Representative examples of arylalkyl include phenylmethyl (i.e. benzyl), phenylethyl, and phenylpropyl.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Arylthio" refers to an aryl group attached to a parent molecular moiety through a sulfur bridge. Examples include phenylthiol. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —CH$_2$CH$_2$NH—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected R$^A$ groups (where R$^A$ is as defined in formula A options (b)-(i)) to complete their valence.

Formula A. The silicone-containing component may comprise one or more polymerizable compounds of Formula A:

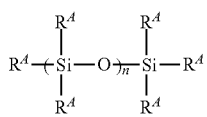

Formula A wherein:

at least one R$^A$ is a group of formula R$_g$-L- wherein R$_g$ is a polymerizable group and L is a linking group, and the remaining R$^A$ are each independently:

a. R$_g$-L-,
b. C$_1$-C$_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof,
c. C$_3$-C$_{12}$ cycloalkyl optionally substituted with one or more alkyl, hydroxy, amino, amido, oxa, carbonyl, alkoxy, amido, carbamate, carbonate, halo, phenyl, benzyl, or combinations thereof,
d. a C$_6$-C$_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof,
e. halo,
f. alkoxy, cyclic alkoxy, or aryloxy,
g. siloxy,
h. alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different R$^A$ substituents and if different R$^A$ substituents are present, then groups may be in random or block configuration.

In Formula A, three R$^A$ may each comprise a polymerizable group, alternatively two R$^A$ may each comprise a polymerizable group, or alternatively one R$^A$ may comprise a polymerizable group.

"Silyl" refers to a structure of formula R$_3$Si— and "siloxy" refers to a structure of formula R$_3$Si—O—, where each R in silyl or siloxy is independently selected from trimethylsiloxy, C$_1$-C$_8$ alkyl (preferably C$_1$-C$_3$ alkyl, more preferably ethyl or methyl), and C$_3$-C$_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[CH$_2$CH$_2$O]$_p$— or CH$_3$O—[CH$_2$CH$_2$O]$_p$—). Examples of alkyleneoxy include polyethyleneoxy, polypropyleneoxy, polybutyleneoxy, and poly(ethyleneoxy-co-propyleneoxy).

"Oxaalkylene" refers to an alkylene group as defined above where one or more non-adjacent CH$_2$ groups have been substituted with an oxygen atom, such as —CH$_2$CH$_2$OCH(CH$_3$)CH$_2$—. "Thiaalkylene" refers to an alkylene group as defined above where one or more non-adjacent CH$_2$ groups have been substituted with a sulfur atom, such as —CH$_2$CH$_2$SCH(CH$_3$)CH$_2$—.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester (—CO$_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —OCF$_2$—, —OCF$_2$CF$_2$—, —OCF$_2$CH$_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy-(where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include C$_1$-C$_8$ alkylene (preferably C$_2$-C$_6$ alkylene) and C$_1$-C$_8$ oxaalkylene (preferably C$_2$-C$_6$ oxaalkylene), each of which is optionally substituted with 1 or 2 groups independently selected from hydroxyl and siloxy. Preferred linking groups also include carboxylate, amide, C$_1$-C$_8$alkylene-carboxylate-C$_1$-C$_8$alkylene, or C$_1$-C$_8$ alkylene-amide-C$_1$-C$_8$ alkylene.

When the linking group is comprised of combinations of moieties as described above (e.g., alkylene and cycloalkylene), the moieties may be present in any order. For instance, if in Formula A above, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg or Pg) to which the linking group is attached. For example, if in Formula A, L is indicated as being alkylene-cycloalkylene, then Rg-L is preferably Rg-alkylene-cycloalkylene-.

The term "electron withdrawing group" (EWG) refers to a chemical group which withdraws electron density from the atom or group of atoms to which the electron withdrawing group is attached. Examples of EWGs include, but are not limited to, cyano, amide, ester, keto, or aldehyde. A preferred EWG is cyano (CN).

The terms "light absorbing compound" refers to a chemical material that absorbs light within the visible spectrum (e.g., in the 380 to 780 nm range). A "high energy radiation absorber," "UV/HEV absorber," "UV/HEV absorbing compound," or "high energy light absorbing compound" is a chemical material that absorbs various wavelengths of ultraviolet light, high energy visible light, or both. A material's ability to absorb certain wavelengths of light can be determined by measuring its UV/VIS transmission spectrum. Compounds that exhibit no absorption at a particular wavelength will exhibit substantially 100 percent transmission at that wavelength. Conversely, compounds that completely absorb at a particular wavelength will exhibit substantially 0% transmission at that wavelength. If the amount of a material's transmission is indicated as a percentage for a particular wavelength range, it is to be understood that the material exhibits the percent transmission at all wavelengths within that range.

When the compounds described herein contain olefinic double bonds or other centers of geometric asymmetry, and unless otherwise specified, it is intended that the compounds include the cis, trans, Z- and E-configurations. Likewise, all tautomeric and salt forms are also intended to be included.

The term "optional substituent" means that a hydrogen atom in the underlying moiety is optionally replaced by a substituent. Any substituent may be used that is sterically practical at the substitution site and is synthetically feasible. Identification of a suitable optional substituent is well within the capabilities of an ordinarily skilled artisan. Examples of an "optional substituent" include, without limitation, $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^4R^5$, benzyl, $SO_3H$, or $SO_3Na$, wherein $R^4$ and $R^5$ are independently H or $C_1$-$C_6$ alkyl. The foregoing substituents may be optionally substituted by an optional substituent (which, unless otherwise indicated, is preferably not further substituted). For instance, alkyl may be substituted by halo (resulting, for instance, in $CF_3$).

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

In some embodiments, the reactive monomer mixture includes at least one polyamide. As used herein, the term "polyamide" refers to polymers and copolymers comprising repeating units containing amide groups. The polyamide may comprise cyclic amide groups, acyclic amide groups and combinations thereof, and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups. Polyamides suitable for use with the presently disclosed compositions and methods are disclosed in U.S. Patent Application Publication No. 20180009922 for SILICONE HYDROGELS COMPRISING HIGH LEVELS OF POLYAMIDES to Alli et al., published Jan. 11, 2018, and U.S. Patent Application Publication No. 20180011222 for SILICONE HYDROGELS COMPRISING POLYAMIDES to Alli et al., published Jan. 11, 2018, each of which are incorporated herein by reference in their entirety.

"Abbe number," also known as the V-number or constringence of a transparent material, is a measure of the material's dispersion, i.e., variation of refractive index versus wavelength, with high values of V indicating low dispersion. The Abbe number of a material is defined as:

$$V_D = \frac{n_D - 1}{n_F - n_C};$$

where $n_D$, $n_F$ and $n_C$ are the refractive indices of the material at the wavelengths of the Fraunhofer D-, F- and C-spectral lines (589.3 nm, 486.1 nm and 656.3 nm respectively).

"Refractive index" is defined as:

$$n = \frac{c}{v};$$

where c is the speed of light in a vacuum and v is the phase velocity of light in the medium.

B. Compositions

In some embodiments, the presently disclosed subject matter provides a composition made by free radical polymerization of a reactive monomer mixture comprising:
  a. at least one low glass transition temperature monomer;
  b. a tricyclo[5.2.1.0$^{2,6}$]decanedimethanol di(meth)acrylate cross-linking agent; and
  c. an ethylene glycol dicyclopentenyl ether (meth)acrylate;
wherein the concentration of the ethylene glycol dicyclopentenyl ether (meth)acrylate in the reactive monomer mixture excluding any diluent is greater than 80 weight percent; and wherein the composition exhibits a refractive index of at least 1.45 and an Abbe number of at least 39 ("Composition (A)".

In some embodiments, the low glass transition temperature monomer is a monomer whose homopolymer exhibits a glass transition temperature lower than 0° C., lower than minus 5° C. (−5° C.), lower than minus 10° C. (−10° C.), lower than minus 15° C. (−15° C.), or lower than minus 20° C. (−20° C.).

In some embodiments, the reactive monomer mixture of Composition (A) comprises at least one low glass transition temperature monomer in amount between about 1 and about 19 weight percent, including about 1, 2, 3, 4, 5, 6, 7, 8, 9, 10, 11, 12, 13, 14, 15, 16, 17, 18, and 19 weight percent, between about 4 and about 17 weight percent, including about 4, 5, 6, 7, 8, 9, 10, 11, 12, 13, 14, 15, 16, and 17 weight percent, between about 6 and about 15 weight percent, including about 6, 7, 8, 9, 10, 11, 12, 13, 14, and 15 weight percent, or between about 8 and about 15 weight percent, including about 8, 9, 10, 11, 12, 13, 14, and 15 weight percent. In some embodiments, the weight percent of the low glass transition temperature monomer in the reactive monomer mixture is calculated excluding a diluent.

Low glass transition temperature monomers can be monomers or macromers. The glass transition temperature of polymers containing the low glass transition temperature monomers is measured by differential scanning calorimetry (DSC) as described herein from the second heating scan.

In some embodiments, the low glass transition temperature monomer is a hydrophilic monomer. In some embodiments, the hydrophilic monomer is a poly(ethylene glycol)-containing monomer. In some embodiments, the poly(ethylene glycol)-containing monomer is selected from poly(ethylene glycol) methyl ether (meth)acrylate and poly(ethylene glycol) (meth)acrylate. In some embodiments, the poly(ethylene glycol)-containing monomer is poly(ethylene glycol) methacrylate. In some embodiments, the poly(ethylene glycol)-containing monomer is poly(ethylene glycol) methyl ether methacrylate. In some embodiments, the reactive monomer mixture of the Composition (A) comprises a combination of poly(ethylene glycol) methacrylate and poly(ethylene glycol) methyl ether methacrylate.

In some embodiments, the poly(ethylene glycol)-containing monomer has a number-average molecular weight ($M_n$) of about 200 g/mol to about 1000 g/mol, including 200 g/mol, 220 g/mol, 240 g/mol, 260 g/mol, 280 g/mol, 300 g/mol, 320 g/mol, 340 g/mol, 360 g/mol, 380 g/mol, 400 g/mol, 420 g/mol, 440 g/mol, 460 g/mol, 480 g/mol, 500 g/mol, 520 g/mol, 540 g/mol, 560 g/mol, 580 g/mol, 600 g/mol, 620 g/mol, 640 g/mol, 660 g/mol, 680 g/mol, 700 g/mol, 720 g/mol, 740 g/mol, 760 g/mol, 780 g/mol, 800 g/mol, 820 g/mol, 840 g/mol, 860 g/mol, 880 g/mol, 900 g/mol, 920 g/mol, 940 g/mol, 960 g/mol, 980 g/mol, and 1000 g/mol. In some embodiments, the poly(ethylene glycol)-containing monomer has a number-average molecular weight ($M_n$) of about 200 g/mol to about 400 g/mol, including 200 g/mol, 220 g/mol, 240 g/mol, 260 g/mol, 280 g/mol, 300 g/mol, 320 g/mol, 340 g/mol, 360 g/mol, 380 g/mol, and 400 g/mol.

In some embodiments, the poly(ethylene glycol)-containing monomer has formula:

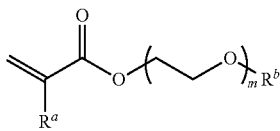

wherein $R^a$ and $R^b$ are each independently selected from hydrogen, methyl, and ethyl and m is an integer from 1 to 25, including 1, 2, 3, 4, 5, 6, 7, 8, 9, 10, 11, 12, 13, 14, 15, 16, 17, 18, 19, 20, 21, 22, 23, 24, and 25. In some embodiments, $R^a$ is hydrogen. In some embodiments, $R^a$ is methyl. In some embodiments, $R^b$ is hydrogen. In some embodiments, $R^b$ is methyl. In some embodiments, $R^b$ is ethyl. In particular embodiments, $R^a$ is methyl and $R^b$ is hydrogen. In some embodiments, $R^a$ is methyl and $R^b$ is methyl. In some embodiments, $R^a$ is hydrogen and $R^b$ is methyl. In some embodiments, $R^a$ is hydrogen and $R^b$ is ethyl. In some embodiments, m is an integer from 1 to 8, including 1, 2, 3, 4, 5, 6, 7, and 8.

In some embodiments, the low glass transition temperature monomer is a hydrophobic monomer. In some embodiments, the hydrophobic monomer is selected from aliphatic (meth)acrylates, haloalkyl (meth)acrylates, cycloaliphatic (meth)acrylates, aromatic (meth)acrylates, and any combination thereof.

In some embodiments, the hydrophobic monomer is an aliphatic (meth)acrylate. In some embodiments, the aliphatic (meth)acrylate comprises a linear or branched alkyl group. In particular embodiments, the aliphatic (meth)acrylate is a $C_2$-$C_{20}$ alkyl acrylate, including $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl acrylate. In other embodiments, the aliphatic (meth)acrylate is a $C_6$-$C_{20}$ alkyl methacrylate, including $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl methacrylate. In some embodiments, the aliphatic (meth)acrylate has at least one alkyl group comprising at least one carbon-carbon double bond. In more particular embodiments, the $C_2$-$C_{20}$ alkyl (meth)acrylate is selected from the group consisting of ethyl acrylate, n-propyl acrylate, n-butyl acrylate, iso-butyl acrylate, n-hexyl (meth)acrylate, 2-ethylhexyl (meth)acrylate, n-octyl (meth)acrylate, 2-propylheptyl (meth)acrylate, n-decyl (meth)acrylate, iso-decyl (meth)acrylate, n-dodecyl (meth)acrylate, and any combination thereof. In yet more particular embodiments, the aliphatic (meth)acrylate comprises a linear alkyl group containing between 6 and 10 carbon atoms (a $C_6$-$C_{10}$ linear alkyl group), including 6, 7, 8, 9, and 10 carbon atoms. In some embodiments, the aliphatic (meth)acrylate is n-hexyl acrylate.

In some embodiments, the hydrophobic monomer is a haloalkyl (meth)acrylate. In some embodiments, the haloalkyl (meth)acrylate comprises a linear or branched haloalkyl group containing between 1 and 20 carbon atoms, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$. In more particular embodiments, the haloalkyl (meth)acrylate is selected from the group consisting of 1H,1H-heptafluorobutyl acrylate, 1H,1H,3H-hexafluorobutyl acrylate, 1H,1H,5H-octafluoropentyl acrylate, 2,2,2-trifluoroethyl acrylate, 1H,1H-heptafluorobutyl acrylate, and any combination thereof.

In some embodiments, the haloalkyl (meth)acrylate is a perhaloalkyl (meth)acrylate. In some embodiments, the perhaloalkyl (meth)acrylate comprises a linear or branched perhaloalkyl group containing between 1 and 20 carbon atoms, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$.

In some embodiments, the hydrophobic monomer is a cycloaliphatic (meth)acrylate. In some embodiments, the cycloaliphatic (meth)acrylate comprises a $C_3$-$C_8$ cycloalkyl group, a $C_3$-$C_7$ cycloalkyl group, a $C_4$-$C_7$ cycloalkyl group, or a $C_5$-$C_6$ cycloalkyl group. In some embodiments, the cycloaliphatic (meth)acrylate comprises at least one cyclic carbon-carbon double bond. In other embodiments, the cycloalkyl group can be substituted with one or more alkyl, hydroxy, amino, amido, oxa, carboxy, alkyl carboxy, carbonyl, alkoxy, amido, carbamate, carbonate, halo, phenyl, benzyl, or combinations thereof. In some particular embodiments, the cycloaliphatic (meth)acrylate is selected from 2-cyclohexylethyl acrylate, 3-cyclohexylpropyl acrylate, 4-cyclohexylbutyl acrylate, and any combination thereof.

In some embodiments, the hydrophobic monomer is an aromatic (meth)acrylate. In some embodiments, the aromatic (meth)acrylate comprises at least one aryl group. In some embodiments, the aryl group is a phenyl group. In some embodiments, the aryl group can be present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2-phenoxyethyl, or 3-phenoxypropyl), or an arylthioalkyl group (e.g., phenylthiomethyl, 2-phenylthioethyl, or 3-phenylthiopropyl). In some particular embodiments, aromatic (meth)acrylate is selected from 2-phenylethyl acrylate, 3-phenylpropyl acrylate, 4-phenylbutyl acrylate, 2-phenoxyethyl acrylate, 3-phenoxypropyl acrylate, 4-phenoxybutyl acrylate, and any combination thereof. In some embodiments, the aromatic (meth)acrylate is 3-phenylpropyl acrylate. In other embodiments, the aromatic (meth)acrylate is 4-phenylbutyl acrylate.

In some embodiments, the tricyclo[5.2.1.0$^{2,6}$]decanedimethanol di(meth)acrylate cross-linking agent is tricyclo[5.2.1.0$^{2,6}$]decanedimethanol diacrylate. In some embodiments, the reactive monomer mixture comprises the tricyclo[5.2.1.0$^{2,6}$]decanedimethanol di(meth)acrylate (e.g., tricyclo[5.2.1.0$^{2,6}$]decanedimethanol diacrylate) in an amount between about 0.5 weight percent and about 10 weight percent (including about 0.5, 1, 2, 3, 4, 5, 6, 7, 8, 9, or 10 weight percent), about 0.5 weight percent and about 5 weight percent (including about 0.5, 1.0, 1.5, 2.0, 2.5, 3.0, 3.5, 4.0, 4.5, or 5.0 weight percent), or about 1 weight percent and about 4 weight percent (including about 1.0, 1.5, 2.0, 2.5, 3.0, 3.5, or 4.0 weight percent). In some embodiments, the weight percent of the tricyclo[5.2.1.0$^{2,6}$]decanedimethanol di(meth)acrylate cross-linking agent (e.g., tricyclo[5.2.1.0$^{2,6}$]decanedimethanol diacrylate) in the reactive monomer mixture is calculated excluding a diluent.

In some embodiments, the ethylene glycol dicyclopentenyl ether (meth)acrylate is ethylene glycol dicyclopentenyl ether acrylate. In some embodiments, the reactive monomer mixture comprises the ethylene glycol dicyclopentenyl ether (meth)acrylate (e.g., ethylene glycol dicyclopentenyl ether acrylate) in an amount between about 80.1 weight percent and about 95 weight percent (including about 80.1, 80.2, 80.3, 80.4, 80.5, 80.6, 80.7, 80.8, 80.9, 81, 82, 83, 84, 85, 86, 87, 88, 89, 90, 91, 92, 93, 94, or 95 weight percent), between about 80.1 weight percent and about 92 weight percent, (including about 80.1, 80.2, 80.3, 80.4, 80.5, 80.6, 80.7, 80.8, 80.9, 81, 82, 83, 84, 85, 86, 87, 88, 89, 90, 91, or 92 weight percent), or between about 80.1 weight percent and about 90 weight percent (including about 80.1, 80.2, 80.3, 80.4, 80.5, 80.6, 80.7, 80.8, 80.9, 81, 82, 83, 84, 85, 86, 87, 88, 89, or 90 weight percent). In some embodiments, the weight percent of the ethylene glycol dicyclopentenyl ether (meth)acrylate (e.g., ethylene glycol dicyclopentenyl ether acrylate) in the reactive monomer mixture is calculated excluding a diluent.

In some embodiments, the reactive monomer mixture of Composition (A) further comprises a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis(meth)acrylamide, poly(ethylene glycol) di(meth)acrylate, bis(2-hydropropyl (meth)acrylate) terminated polydimethylsiloxanes, and any combination thereof.

In some embodiments, the reactive monomer mixture of Composition (A) further comprises a hydroxyalkyl (meth)acrylate monomer. In some embodiments, the hydroxyalkyl (meth)acrylate comprises a linear, branched, or cyclic hydroxyalkyl group having between 1 and carbon atoms (a $C_1$-$C_{25}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$. In some embodiments, the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof. In some particular embodiments, the hydroxyalkyl (meth)acrylate monomer is 2-hydroxyethyl acrylate.

In some embodiments, the reactive monomer mixture further comprises an alkoxyalkyl (meth)acrylate. In some embodiments, the alkoxyalkyl (meth)acrylate comprises a linear, branched, or cyclic alkoxyalkyl group having between 1 and 25 carbon atoms (a $C_1$-$C_{25}$ alkoxyalkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$ and at least one oxygen atom.

In some embodiments, the reactive monomer mixture further comprises an amide-containing monomer selected from the group consisting of vinyl pyrrolidone, N-vinyl-N-methyl acetamide, N-methyl methacrylamide, N-vinyl acetamide, N,N-dimethyl acrylamide, N-hydroxy ethylacrylamide, N-(2-hydroxypropyl)acrylamide, N-(3-hydroxypropyl)acrylamide, N-(2-hydroxyethyl)(meth)acrylamide, N-(2-hydroxypropyl)(meth)acrylamide, and N-(3-hydroxypropyl)(meth)acrylamide, and any combination thereof.

In some embodiments, the reactive monomer mixture further comprises a polymer derived from an amide-containing monomer. In some embodiments, the polymer derived from an amide-containing monomer is selected from poly(vinyl pyrrolidone), poly(N-vinyl-N-methyl acetamide), poly(N-vinyl acetamide), poly(dimethyl acrylamide), and a copolymer or a mixture thereof. In particular embodiments, the polyamide is poly(vinyl pyrrolidone). In certain embodiments, the polymer derived from an amide-containing monomer is a copolymer. In some embodiments, the reactive monomer mixture comprises the polymer derived from an amide-containing monomer in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the polymer derived from an amide-containing monomer present in the reactive monomer mixture is calculated excluding a diluent.

In some embodiments, the reactive monomer mixture of Composition (A) further comprises a UV/HEV absorbing compound.

In some embodiments, the UV/HEV absorbing compound may take the form of Formula

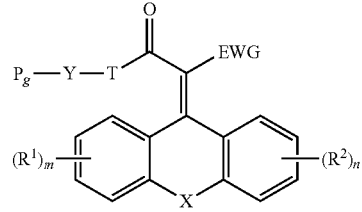

Formula I wherein:

m and n are independently 0, 1, 2, 3, or 4;

T is a bond, O, or NR;

X is O, S, NR, SO, or SO$_2$;

Y is a linking group;

P$_g$ is a polymerizable group;

R at each occurrence is independently H, C$_1$-C$_6$ alkyl, cycloalkyl, heterocycloalkyl, aryl, heteroaryl, or Y—P$_g$;

R$^1$ and R$^2$, when present, are independently at each occurrence C$_1$-C$_6$ alkyl, C$_1$-C$_6$alkoxy, C$_1$-C$_6$ thioalkyl, C$_3$-C$_7$ cycloalkyl, aryl (preferably unsubstituted phenyl or phenyl substituted with alkyl or halo), halo, hydroxy, amino, NR$^3$R$^4$, or benzyl, wherein R$^3$ and R$^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

Compounds of Formula I preferably contain one or two Y—$P_g$ groups. More preferably, the compounds contain one Y—$P_g$ group.

In certain embodiments, the UV/HEV absorbing compound is a compound of Formula I, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof. In certain embodiments, the UV/HEV absorbing compound is 2-(2-cyano-2-(9H-thioxanthen-9-ylidene)acetamido)ethyl methacrylate. In certain embodiments, the UV/HEV absorbing compound is 3-(3-(tert-butyl)-5-(5-chloro-2H-benzo[d][1,2,3]triazol-2-yl)-4-hydroxyphenyl)propyl methacrylate.

In some embodiments, the reactive monomer mixture of Composition (A) comprises at least one UV/HEV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including about 1, 2, and 3 weight percent. In some embodiments, the weight percent of the at least one UV/HEV absorbing compound present in the reactive monomer mixture is calculated excluding a diluent.

In some embodiments, the reactive monomer mixture of Composition (A) further comprises at least one hydroxy silicone component. The hydroxy silicone component can be a monomer, macromer, prepolymer, or crosslinking agent. In certain embodiments, the hydroxy silicone monomer is selected from 3-(3-(1,1,1,3,5,5,5-heptamethyltrisiloxan-3-yl)propoxy)-2-hydroxypropyl methacrylate (SiMAA), mono-n-butyl terminated monomethacryloxypropyl terminated polydimethylsiloxane (mPDMS), and mono-(2-hydroxy-3-methacryloxypropyl)-propyl ether terminated mono-n-butyl terminated polydimethylsiloxane (OH-mPDMS), and any combination thereof.

In some embodiments, the hydroxy silicone cross-linking agent has the chemical formula:

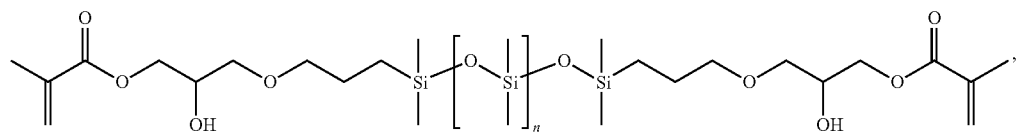

wherein n is an integer from 5 to 50, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In some embodiments, n is 15, 16, 17, 18, 19, 20, 21, 22, 23, 24, or 25. In particular embodiments, n is 20.

In some embodiments, the reactive monomer mixture of Composition (A) further comprises at least one diluent.

In some embodiments, Composition (A) has a water content of between about 0 weight percent and about 15 weight percent, between about 1 weight percent and about 10 weight percent, or between about 1 weight percent and about 5 weight percent. In some embodiments, the water content is measured when the material is hydrated at 37° C.

In some embodiments, the Composition (A) has a refractive index of at least 1.45 and an Abbe number of at least 45. In other embodiments, Composition (A) has a refractive index of at least 1.48 and an Abbe number of at least 50. In yet other embodiments, Composition (A) has a refractive index of at least 1.50 and an Abbe number of at least 50. In some embodiments, the indicated refractive index and the indicated Abbe number are measured when the material is in a dry state at 25° C.

In some embodiments of Composition (A), the free radical polymerization is a photopolymerization using a bisacylphosphine oxide initiator. In some embodiments, the initiator is bis(2,4,6-trimethylbenzoyl)-phenylphosphineoxide. In other embodiments, the free radical polymerization is initiated using a thermal initiator. In some embodiments, the thermal initiator is 1,1'-azobisisobutyronitrile.

C. Ophthalmic Devices

In some embodiments, the presently disclosed subject matter provides a device comprising Composition (A) as described immediately hereinabove.

In particular embodiments, the ophthalmic device comprises a lens, inlay, outlay, or insert selected from an intraocular implant or lens, a contact lens, a corneal inlay, a corneal outlay, and a corneal insert.

In specific embodiments, the ophthalmic device is an intraocular implant or lens. More specifically, the presently disclosed subject matter also provides intraocular implants and/or lenses made at least partially or completely from the compositions described herein. Such intraocular implants or lenses can include an optic portion and one or more haptic portions. Typically, the compositions of the presently disclosed subject matter will make up part or all of the optic portion of the intraocular implant or lens. In some embodiments, the optic portion of the implant or lens will have a core made from one of the compositions described herein surrounded by different polymer or material. Implants or lenses in which the optic portion is made up of at least partially of one of the compositions of the presently disclosed subject matter will usually also have a haptic portion. The haptic portion can also be made of polymer of the disclosure or can be made of a different material, for example another polymer.

In some embodiments, the intraocular implant or lens of the presently disclosed subject matter is a one-piece lens having a soft, foldable central optic region and an outer peripheral region (haptic-region) in which both regions are made of the same polymer. In other embodiments, the optic and haptic regions can be formed from different types of polymers or materials, if desired. Some implants or lenses can also have haptic portions that are made up of different materials, for example where one or more haptic portions is made from the same material as the optic portion and other haptic portions are made of materials other than a polymer of the disclosure. Multicomponent implants or lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The compositions described herein have been designed so that they are capable of being folded so that the intraocular lens can be inserted into the eye of an individual through a small incision. In some instances that incision will be less than 2.5 mm; in some instances that incision will be less than 2 mm. The haptic portion of the lens provides the required support for the implant or lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

The optic portion of the intraocular lens can be approximately 2-6 mm in diameter prior to hydration. The 2-6 mm diameter is fairly standard in the art and is generally chosen to cover the pupil in its fully dilated state under naturally occurring conditions. However, other sizes are contemplated and the presently disclosed subject matter is not limited to any particular diameter or size of intraocular lens. Furthermore, it is not necessary that the lens optic portion be circular; it could also be oval, square, or any other shape as desired.

The intraocular lens can further include one or more non-optical haptic components extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Should the intraocular lens include other components besides the optical and haptic portions, such other portions can be made of a polymer as are the haptic and optic portions, or if desired, another material.

The intraocular implants lenses may be inserted into the eye in any manner known in the art. For example, the intraocular lens may be folded prior to insertion into the eye using an intraocular lens inserter or by small, thin forceps of the type typically used by ophthalmic surgeons. After the implant or lens is in the targeted location, it is released to unfold. As is well known in the art, typically the lens that is to be replaced is removed prior to insertion of the intraocular lens. The intraocular lens of the presently disclosed subject matter can be made of a generally physiologically inert soft polymeric material that is capable of providing a clear, transparent, refractive lens body even after folding and unfolding. In some embodiments, the foldable intraocular lens of the presently disclosed subject matter can be inserted into any eye by injection whereby the mechanically compliant material is folded and forced through a small tube such as a 1 mm to 3 mm inner diameter tube.

D. Method for Making an Ophthalmic Device

In still yet other embodiments, the presently disclosed subject matter provides a method for making an ophthalmic device, the method comprising: (a) providing any of the compositions described herein (e.g., Composition (A)) and (b) forming an ophthalmic device. In other embodiments, the presently disclosed subject matter provides a method for making an ophthalmic device, the method comprising: (a) preparing a blank from any of the compositions described herein (e.g., Composition (A)) and (b) machining an ophthalmic device from the blank. In still other embodiments, the presently disclosed subject matter provides a method for making an ophthalmic device, the method comprising molding an ophthalmic device from any of the compositions described herein (e.g., Composition (A)). In still other embodiments, the presently disclosed subject matter provides a method for making an ophthalmic device, the method comprising molding an ophthalmic device from any of the inventive compositions described herein, and then refining the surface via lathing. In certain embodiments of the above methods, the method further comprises the step of extracting the ophthalmic device with a solvent. In certain embodiments, the method further comprises the step of hydrating the extracted ophthalmic device with at least one aqueous solution. In particular embodiments, the method further comprises an irradiation step using a laser, which in certain embodiments, is a two photon laser, which in more certain embodiments, is a femtosecond two photon laser. In more particular embodiments, the method further comprises a step of sterilizing the ophthalmic device. The ophthalmic device may be sterilized by known means such as, but not limited to, autoclaving.

Some embodiments of the disclosure will now be described in detail in the following Examples.

EXAMPLES

Unless otherwise noted, test samples for refractive index, Abbe number, water content and glass transition temperature were polymer buttons that had been extracted with acetonitrile or 2-propanol and dried. Unless otherwise noted, test samples for micro-glistening and macro-glistening testing were lenses.

Refractive Index Test Method: Refractive index was measured using an Anton Paar Abbemat WR-wavelength refractometer. The instrument was equilibrated at either 25° C. or 35° C. for a minimum of 1 hour prior to use. The measurement wavelength was set at 589.3 nanometers. Using a pair of tweezers, the sample was placed on the quartz plate. The instrument lid was closed, and the refractive index was recorded after 60 seconds of dwell time. Measurements were performed on three polymer buttons, and the average was reported. In some examples, where it is noted, measurements were performed on both sides of the three polymer buttons, and the average of the six measurements was reported.

Abbe Number Test Method: Following the steps for measuring the refractive index at 589.3 nm, the refractive index at 486.1 nm and 656.3 nm were determined. Measurements were performed on three polymer buttons, and for each polymer button, the refractive index measurements at all three wavelengths were completed before measuring the next replicate. The Abbe number was calculated as follows:

$$V_D = \frac{n_D - 1}{n_F - n_C};$$

where $n_D$, $n_F$ and $n_C$ are the refractive indices of the material at the wavelengths of the Fraunhofer D-, F- and C-spectral lines (589.3 nm, 486.1 nm and 656.3 nm respectively). The average of the three measurements was reported. In some examples, where it is noted, measurements were performed on both sides of the three polymer buttons, and the average of the six measurements was reported.

Water Content Test Method: The water content was determined gravimetrically. In this method, three dry polymer disks were individually weighed and transferred to individual glass scintillation vials using sharp-tipped metal tweezers. About 10 mL of HPLC grade water was transferred into each vial, and the samples were incubated at 37° C. for 14 days. After incubation, the polymer disks were removed from the vials using a sharp-tipped metal tweezers and briefly blotted on all sides (flat surfaces and edge) using lint-free blotting paper to remove surface/excess water. Using a dry tweezers, each polymer disk was placed in a tared weighing pan and weighed individually. The water content of the polymer disk was calculated as follows: (% WC)=(wet weight−dry weight)/wet weight×100. The average and standard deviation of the water content were calculated, and the average value reported as the percent water content of the disk.

Glass Transition Temperature Test Method: Because of the thickness and/or brittleness of the polymer buttons, test samples were cut from the center of the polymer buttons or lenses using a razor blade. The samples could not be punched out as with a thin film. Test samples were analyzed (in duplicate) on a DSC Q2000 TA instrument at heating rates of 10° C./minute and cooling rates of 5° C./minute under a nitrogen gas atmosphere. The glass transition temperatures were determined from the first and second heating scans ($1^{st}$ scan and $2^{nd}$ scan, respectively).

Micro-Glistening Test Method: Prior to conditioning lenses for dark field light microscopy, lenses were extracted in acetonitrile or methanol. For the extraction, lenses were placed individually into lens cases containing 3 mL of acetonitrile or methanol and extracted overnight at ambient temperature, followed by 3 exchanges of 3 mL aliquots of acetonitrile or methanol at 4 hours interval. After the final extraction, lenses were air dried at ambient temperature for at least six days. Lenses were subsequently cleaned to remove any noticeable residual debris from their fabrication and extraction processes, and then immersed in 0.9% saline solution in fluid cells. Microvacuoles may be induced by placing these cells into an oven at 35° C. for a period of about 15 hours. The lenses were removed from the oven and equilibrated at room temperature for at least 2 hours before being analyzed by dark field light microscopy as described in Biomedical Optics Express, 2013, Vol. 4 No. 8, which is incorporated herein by reference in its entirety. Any standard light microscope or camera capable of dark field imaging may be used. Under dark field settings, the intraocular lens is retro-illuminated with an annulus of light under an oblique angle. If there are no microvacuoles or other light scattering centers, the image is black. As the number of microvacuoles increases, the amount of forward scattered light increases, creating a constellation pattern of forward scattered light on a dark background. The Image J program (or another similar post-image processing software program) was used to determine the density of the microvacuoles from dark field microscopy photographs for small populations of microvacuoles. A circular area with a diameter of 4 millimeter was examined, and the density of microvacuoles calculated (number of microvacuoles or micro-glistenings per millimeter$^2$ (#/mm$^2$)). Generally speaking, intraocular lenses with fewer microvacuoles or micro-glistenings provide better vision than ones with more forward scattering and therefore are preferred. Micro-glistening densities of approximately 4/mm$^2$ are considered low and comparable with intraocular lenses not associated with any glistenings.

Macro-Glistening Test Method: Lenses were placed individually into lens cases containing 3 mL of acetonitrile (ACN). Lenses were extracted at ambient temperature for four hours. The acetonitrile was removed with a disposable pipet, and another 3 mL of acetonitrile was added. The lenses were then extracted overnight at ambient temperature. The acetonitrile was removed with a disposable pipet, and another 3 mL of acetonitrile was added. Lenses were extracted at ambient temperature for four hours. The acetonitrile was removed with a disposable pipet, and another 3 mL of acetonitrile was added. Lenses were extracted at ambient temperature for four hours. The acetonitrile was removed with a disposable pipet, and lenses were air dried at ambient temperature for at least six days. The air-dried lenses were placed individually into lens cases containing 3 mL of methanol and equilibrated at ambient temperature overnight. Alternatively, lenses were initially extracted directly with 3 mL aliquots of methanol overnight, followed by 3 exchanges of 3 mL aliquots of methanol at 4 hours interval. After organic extraction by either method, the lenses were subsequently stepped down into DPBS solution by the following "gradient equilibration" procedure: (1) lenses were placed individually into lens cases containing 3 mL of 80% (v/v) aqueous methanol at ambient temperature for four hours, (2) the 80% (v/v) aqueous methanol was then replaced with 3 mL of 60% (v/v) aqueous methanol at ambient temperature for four hours, (3) the 60% (v/v) aqueous methanol lenses was then replaced with 3 mL of 50% (v/v) methanol:DPBS at ambient temperature overnight, (4) the 50% (v/v) methanol:DPBS was then replaced with 3 mL of 40% (v/v) methanol:DPBS at ambient temperature for four hours, (5) the 40% (v/v) methanol:DPBS was then replaced with 3 mL of 20% (v/v) methanol:DPBS at ambient temperature for four hours, and finally (6) the 20% (v/v) methanol:DPBS was replaced with 3 mL of DPBS at ambient temperature overnight, after at least two rinsing steps with 3 mL of DPBS to remove methanol before equilibrating in DPBS overnight. Vacuoles which scatter light were created in test lenses (as fabricated without extraction, after acetonitrile extraction followed by drying only, or after organic extraction and gradient equilibration) by placing the test lenses individually in lens cases containing 3 mL of PBS. After screwing on the caps, the cases were placed in an incubator at 37° C. for at least three days. Thereafter, the lenses were evaluated by darkfield microscopy using a (Nikon SMZ1500) microscope at 25×-30× magnification. When the number of macro-glistenings is small, they can be counted.

The following abbreviations will be used throughout the Examples and have the following meanings:
TL03 lights: Phillips TLK 40 W/03 bulbs
LED: light emitting diode
RMM: reactive monomer mixture(s)
RI (25): refractive index measured at 25° C.
RI (35): refractive index measured at 35° C.
Abbe # (25): Abbe number measured at 25° C.
Abbe # (35): Abbe number measured at 35° C.
$T_g$: glass transition temperature (° C.) as determined by differential scanning calorimetry (DSC)
mm: millimeter(s)
cm: centimeter(s)
micrometer(s)
nm: nanometer(s)
μL: microliter(s)
mW: milliwatt(s)

g/mol: grams/mole
Da or Dalton(s): gram(s)/mole
kDa: kilodalton(s)
rpm: revolutions per minute
PBS: phosphate buffered saline
DPBS: Dulbecco phosphate buffered saline which contains no calcium or magnesium ions
ACN: acetonitrile
CHA: cyclohexyl acrylate [CAS 3066-71-5] (TCI or Alfa Aesar)
EGDCA: Ethylene glycol dicyclopentenyl ether acrylate [CAS 65983-31-5] (Sigma-Aldrich)

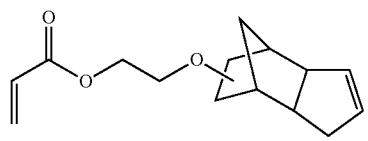

BCHA: ((1R,2S,4R)-bicyclo[2.2.1]hept-5-en-2-yl)methyl acrylate or cyclol acrylate or [(1S,4S)-2-bicyclo[2.2.1]hept-5-enyl]methyl prop-2-enoate [CAS 95-39-6] (Monomer-Polymer and DAJAC Labs Inc.)

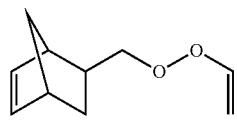

CAA: cinnamyl acrylate

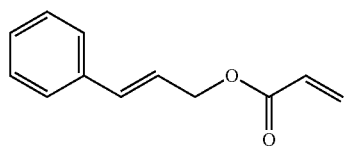

NHA: n-hexyl acrylate [CAS 2499-95-8] (Sigma-Aldrich)
PEA: 2-phenylethyl acrylate [CAS 3530-36-7] (MPD)
PEMA: 2-phenylethyl methacrylate [CAS 3683-12-3]
PPA: 3-phenylpropyl acrylate [CAS 85909-41-7]
TCDA: Tricyclo[5.2.1.0$^{2,6}$]decanedimethanol diacrylate or dimethylol tricyclo decane diacrylate [CAS 42594-17-2] (Sigma-Aldrich or Kyoeisha Chemical Co.)

DMA: N, N-dimethylacrylamide [CAS 2680-03-7] (TCI or Sigma-Aldrich)
NVP: N-vinylpyrrolidin-2-one
HEMA: 2-hydroxyethyl methacrylate (Bimax)
HBA: 4-hydroxybutyl acrylate [CAS 2478-10-6] (TCI or BASF) mPEG 300: poly(ethylene glycol) methyl ether methacrylate ($M_n$=300 grams/mole) (Sigma-Aldrich)

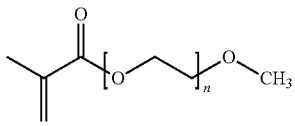

PEG-OH 200: poly(ethylene glycol) methacrylate (Polysciences; molecular weight of the PEG block is 200 grams/mole)
PEG-OH 360: poly(ethylene glycol) methacrylate ($M_n$=360 grams/mole) (Sigma-Aldrich)

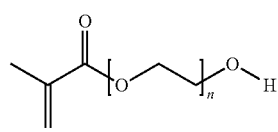

PVP K90: poly(N-vinylpyrrolidone) [CAS 9003-39-8] (Ashland)
PDMA: polydimethylacrylamide ($M_n$=414 kDa; $M_w$=498 kDa; Toray)

The molecular weight was determined by Size Exclusion Chromatography with Multi-Angle Light Scattering (SEC-MALS). The SEC-MALS setup employed aqueous acetonitrile solution as the mobile phase composed of 80% (v/v) 50 mM $Na_2SO_4$ and 20% (v/v) acetonitrile at a flow rate of 0.5 mL/min at 40° C. Two Tosoh Biosciences TSK-gel columns in series were used [SuperAW4000 and SuperAW5000] with an online Agilent 1200 UV/VIS diode array detector, a Wyatt Optilab rEX interferometric refractometer, and a Wyatt mini-DAWN Treos multiangle laser scattering (MALS) detector (λ=658 nm). Absolute molecular weights and polydispersity data were calculated using the Wyatt ASTRA VI SEC/LS software package. About 40 milligrams of PDMA were dissolved in packing solution in a 10 mL volumetric flask. Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask. Three different solutions were prepared and tested. Monomeric serum albumin samples were also tested using solutions made from only 10 milligrams of protein in 10 mL of packing solution. All solutions were filtered through a 0.45-micron nylon membrane filter prior to injection into the SEC-MALS system. The number average molecular weight of the three samples was 414 kDa (standard deviation 12 kDa); the weight average molecular weight of the three samples was 498 kDa (standard deviation 11 kDa); resulting in a polydispersity index of 1.2.

Omnirad 819: bis(2,4,6-trimethylbenzoyl)-phenylphosphineoxide [CAS 162881-26-7] (IGM Resins)
AIBN: azobisisobutyronitrile [CAS 78-67-1]
mPDMS: mono-n-butyl terminated monomethacryloxypropyl terminated polydimethylsiloxane ($M_n$=500-1500 Daltons) (Gelest)
SiMAA: 2-propenoic acid, 2-methyl-2-hydroxy-3-[3-[1,3,3,3-tetramethyl-1-[(trimethylsilyl)oxy]disiloxanyl]propoxy] propyl ester (Toray) or 3-(3-(1,1,1,3,5,5,5-heptamethyltrisiloxan-3-yl)propoxy)-2-hydroxypropyl methacrylate
HO-mPDMS: mono-n-butyl terminated mono-(2-hydroxy-3-methacryloxypropyloxy)-propyl terminated polydimethylsiloxane ($M_n$=1400 Daltons, n=15) (Ortec or DSM-Polymer Technology Group)

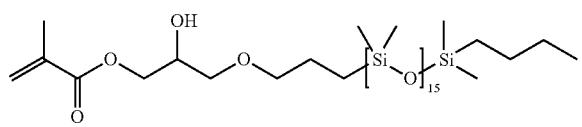

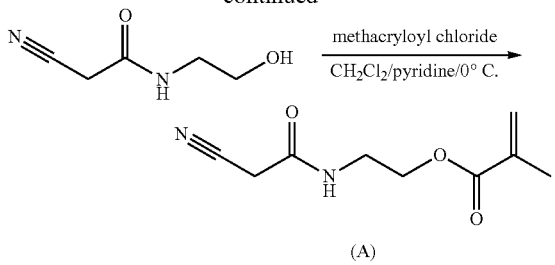

EGDMA: ethylene glycol dimethacrylate (Esstech)
ac-PDMS: bis-3-acryloxy-2-hydroxypropyloxypropyl polydimethylsiloxane (Tegomer V-Si 2250 from Evonik)
XLMA: bis-3-methacryloxy-2-hydroxypropyloxypropyl polydimethylsiloxane ($M_n$=2000 Daltons, n=20) (Shin Etsu)

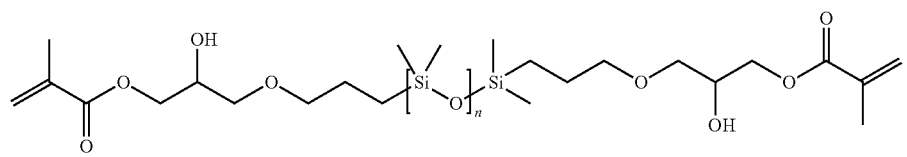

UV-HEV or UV/HEV: ultraviolet and/or high energy visible light
UVB: 3-(3-(tert-butyl)-5-(5-chloro-2H-benzo[d][1,2,3]triazol-2-yl)-4-hydroxyphenyl)propyl methacrylate or 2-Methylacrylic acid, 3-[3-tert-butyl-5-(5-chlorobenzotriazol-2-yl)-4-hydroxyphenyl]-propyl ester (Adesis)

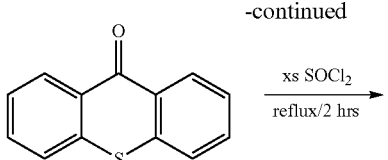

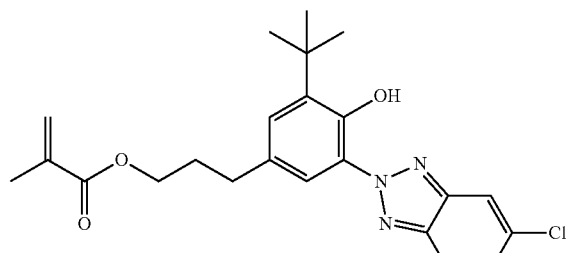

HEVB: 2-(2-cyano-2-(9H-thioxanthen-9-ylidene)acetamido)ethyl methacrylate

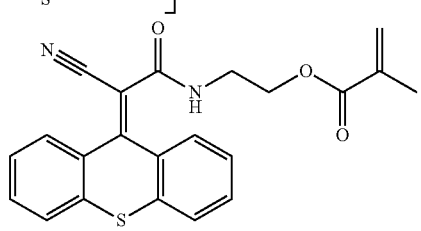

(A)

-continued

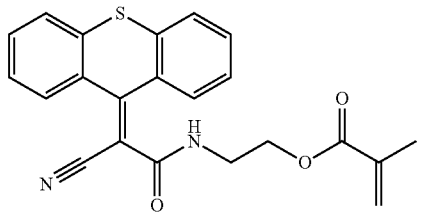 [SMILES: C=C(C)C(=O)OCCNC(=O)C(C#N)=C1c2ccccc2Sc2ccccc21]

Preparation of HEVB: The synthesis of 2-(2-cyano-2-(9H-thioxanthen-9-ylidene)acetamido)-ethyl methacrylate (B) is shown in Scheme 1.

Scheme 1

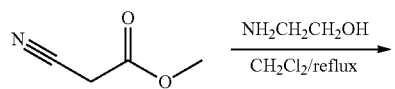

(B)

Methyl cyanoacetate (40 grams, 0.4037 mole) and 25 mL of dichloromethane were stirred in a 3 neck, 500 mL round bottom flask under equipped with a reflux condenser under a nitrogen environment. 2-aminoethanol (23.8 grams, 0.3897 mole, ~0.97 eq.) was added to the solution via an addition funnel, after which the temperature rose and the methylene chloride began to reflux. After the exotherm ceased, external heat was applied to continue a gentle reflux for a total of two hours, after which no ethanolamine was observed by thin layer chromatography.

The reaction may also be conducted at room temperature and is complete within a few hours.

The mixture was cooled to room temperature and all the methylene chloride was evaporated at reduced pressure. The residual oil was washed three times with 50 mL of ethyl acetate to remove unreacted starting material and non-polar impurities. The residual ethyl acetate was then removed under reduced pressure, and the resulting oil was used for acylation without any further purification.

The crude N-2-hydroxyethylacetamide derivative was dissolved in 150 mL of dichloromethane containing 40 grams of pyridine (~0.5 mole) in a three-neck round bottom flask equipped with a reflux condenser, an addition funnel, and a magnetic stirring bar. The flask was immersed in an ice bath and allowed to cool down to around 0° C. Methacryloyl chloride (45.76 grams, ~0.44 mole) was added dropwise from the addition funnel, and the resulting reaction mixture was allowed to warm up to room temperature while constantly stirring the system. Methanol (20 mL) was the added to the flask to quench any unreacted methacryloyl chloride. The volatile components were removed by rotary evaporation under reduced pressure, and the crude product dissolved in 800 mL of dilute aqueous HCl. The resulting aqueous solution was extracted three times with 100 mL of hexanes in a separatory funnel to remove any non-polar impurities. The organic layers were discarded. Sodium chloride was added to the aqueous layer which was then extracted three times with 300 mL of ethyl acetate. About 50 milligrams of BHT were added to the combined organic fractions as an inhibitor, and the ethyl acetate removed by rotary evaporation under reduced pressure. The crude product crystalized out of solution during solvent removal. When about 100 mL of ethyl acetate was left in the flask, 250 mL of hexanes was added, and the crude product was isolated by vacuum filtration using a fritted glass funnel. Thin layer chromatography indicated the presence of a single compound. The filter cake was washed two times with 150 mL of hexanes and then vacuum dried at 40° C., yielding 53 grams (about 70% yield) of 2-(2-cyanoacetamido)ethyl methacrylate (A). $^1$H NMR (500 MHz, CDCl$_3$) δ 1.93 (3H, s, CH$_3$), 3.36 (2H, s, CNCH$_2$), 3.60 (2H, dd, CH$_2$NH), 4.26 (2H, t, CH$_2$OC=O), 5.59 (1H, m, vinylic), 6.11 (1H, bs, vinylic), 6.52 (1H, bs, NH).

A mixture of 9H-thioxanthene-9-one (2.12 grams, 0.01 mole) and thionyl chloride (5 mL, 8.2 grams, ~0.07 mole) was refluxed in a 50 mL round bottom flask under a nitrogen atmosphere with constant stirring. After two hours, the red solution was evaporated to dryness ensuring that all unreacted thionyl chloride was removed from the system. 2-(2-Cyanoacetamido)ethyl methacrylate (A) (2.3 grams, 0.0117 mole, ~1.17 eq.) and 15 mL of dichloromethane were added, and the resulting reaction mixture was heated to reflux under a nitrogen blanket. The reaction was monitored by thin layer chromatography. After two hours, no changes were observed in the chromatogram, so the reactive mixture was allowed to cool down to room temperature. 2-(2-cyano-2-(9H-thioxanthen-9-ylidene)acetamido)ethyl methacrylate (B) was isolated as yellow crystals (3.2 grams, 82% yield) after passing through a short silica gel column (CH$_2$Cl$_2$, followed by 8 weight % EtOAc in CH$_2$Cl$_2$). $^1$H NMR (500 MHz, CDCl$_3$) δ 1.84 (3H, s, CH$_3$), 3.47 (2H, m, CH$_2$NH), 4.01 (2H, t, CH$_2$OC=O), 5.55 (1H, m, vinylic), 5.91 (1H, bs, NH), 5.98 (1H, bs, vinylic), 7.24 (1H, t, Ar—H), 7.31 (1H, t, Ar—H), 7.39 (2H, m, Ar—H), 7.49 (1H, d, Ar—H), 7.55 (1H, m, Ar—H), 7.61 (1H, d, Ar—H), 8.04 (1H, m, Ar—H).

CHMA: Cyclohexylmethyl Acrylate

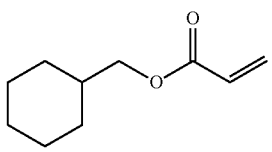

CHEA: 2-Cyclohexylethyl Acrylate

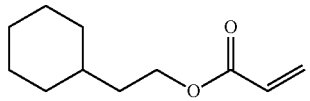

CHPA: 3-Cyclohexylpropyl Acrylate

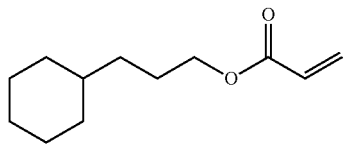

Synthesis of Cyclohexylmethyl Acrylate (CHMA): Cyclohexyl methanol (25.0 g, 219.0 mmol) and triethyl amine (33.46 g, 330.7 mmol) were dissolved in dichloromethane (450 mL) and cooled to about 0° C. using an ice bath. Acryloyl chloride (29.74 g, 328.5 mmol) was added over a period of 20 minutes while maintaining a constant temperature of about 0° C. After the addition was complete, the reaction mixture was stirred at 0° C. for 30 minutes followed by stirring at ambient temperature overnight. Thin layer chromatography was used to monitor the progress of the reaction. When the reaction was complete, triethyl ammonium chloride was filtered off; dissolved in deionized water (200 mL) and extracted with dichloromethane (3×50 mL). The combined filtrate and organic extracts were washed with water (2×50 mL), brine (25 mL), dried over anhydrous Na$_2$SO$_4$, vacuum filtered, and concentrated by rotary evaporation. The crude product was then passed through a short plug of silica gel, eluting with 10% ethyl acetate in n-hexanes, to afford the desired product CHMA as a clear oil (98% yield). $^1$H-NMR (500 MHz, CDCl$_3$): δ 6.39 (1H, dd, J=1.0, 17.0 Hz), 6.12 (1H, dd, J=10.0, 17.0 Hz), 5.81 (1H, dd, J=1.5, 10.0 Hz), 3.97 (2H, d, J=6.0 Hz), 1.76-1.62 (6H, m), 1.31-1.15 (3H, m), 0.95-1.01 (2H, m).

Synthesis of 2-Cyclohexylethyl Acrylate (CHEA): 2-Cyclohexylethyl acrylate was prepared by the same general procedure except that 2-cyclohexyl ethanol was used instead of cyclohexyl methanol (99% yield). $^1$H-NMR (500 MHz, CDCl$_3$): δ 6.38 (1H, dd, J=1.1, 17.2 Hz), 6.11 (1H, dd, J=10.1, 17.2 Hz), 5.80 (1H, dd, J=1.4, 10.1 Hz), 4.18 (2H, t, J=7.0 Hz), 1.74-1.62 (5H, m), 1.58-1.54 (2H, m), 1.39-1.36 (1H, m), 1.27-1.13 (3H, m), 0.97-0.90 (2H, m).

Synthesis of 3-Cyclohexylpropyl Acrylate (CHPA): 3-Cyclohexylpropyl acrylate was prepared by the same general procedure except that 3-cyclohexyl propanol was used instead of cyclohexyl methanol (99% yield). $^1$H-NMR (500 MHz, CDCl$_3$): δ 6.40 (1H, dd, J=1.0, 17.1 Hz), 6.11 (1H, dd, J=10.0, 17.1 Hz), 5.81 (1H, dd, J=1.5, 10.0 Hz), 4.13 (2H, t, J=7.1 Hz), 1.71-1.64 (7H, m), 1.25-1.20 (6H, m), 0.91-0.88 (2H, m).

Examples 1-3

Under yellow lighting, RMMs listed in Table 1 were degassed using vacuum for at least 7 minutes, back filling the head-space with nitrogen gas, and then immediately transferred into a fill box having a nitrogen gas atmosphere with 0.1% to 0.5% (v/v) oxygen gas and an internal temperature at ambient temperature. Polymer disks (about 0.75 millimeters in thickness and 12-14 millimeters in diameter)

were fabricated using circular plastic molds made of polypropylene. About 250 microliters of RMM were dispensed into the mold assembly, and the assembly was transferred into a cure box held at a temperature between 60° C. and 65° C. and then cured using TL03 lights having an intensity of 6-7 mW/cm² for 90 minutes. The cured assemblies were manually demolded. The polymer disks were all transparent and exhibited low levels of surface tackiness. Each disk was extracted with 2-propanol and subsequently dried using the following steps: (a) one disk was transferred into a glass jar with 20 mL solvent and shaken at 115 rpm for 24 hours at 50° C. using an incubator/shaker, (b) the solvent was completely decanted, replaced with fresh 20 mL aliquot of 2-propanol, and shaken at 115 rpm for 1.5 hours at 50° C., (c) step (b) was repeated two more times, (d) after the final solvent decant, the polymer disk was allowed to air dry at room temperature overnight, and then (e) the disk was placed in a vacuum oven at 60-65° C. for seven days (less than one inch of mercury). For each example, multiple disks were prepared. The refractive index, Abbe number, and water content were determined on the dried disks. The average refractive indexes, Abbe numbers, and water contents are listed in Table 2. Standard deviations are reported within the parentheses.

TABLE 1

| Formulations | | | |
|---|---|---|---|
| Components (weight %) | Ex. 1 | Ex. 2 | Ex. 3 |
| EGDCA | 80.1 | 85 | 90 |
| TCDA | 2 | 4 | 1.5 |
| PEG—OH 360 | 16.97 | 10.07 | 7.57 |
| UVB | 0.7 | 0.7 | 0.7 |
| Omnirad 819 | 0.23 | 0.23 | 0.23 |

TABLE 2

| Physical Properties | | |
|---|---|---|
| | Average Refractive Index | Average Abbe Number | Average Water Content (weight percent) |
|---|---|---|---|
| Ex. 1 | 1.523779 (0.000417) | 54.52 (0.29) | 2.80% (0.000503) |
| Ex. 2 | 1.527631 (0.000380) | 52.47 (0.31) | 0.97% (0.000361) |
| Ex. 3 | 1.528784 (0.000138) | 52.04 (0.24) | 0.86% (0.000989) |

Examples 1-3 exhibited both high refractive index (greater than 1.50) and high Abbe number (greater than 50) making these materials suitable for ophthalmic devices such as intraocular lenses. Examples 1-3 also exhibited low water content which can provide dimensional stability for implantable ophthalmic devices.

Examples 4-6

Under yellow lighting, RMMs listed in Table 3 were degassed using vacuum for at least 7 minutes, back filling the head-space with nitrogen gas, and then immediately transferred into a fill box having a nitrogen gas atmosphere with 0.1% to 0.5% (v/v) oxygen gas and an internal temperature at ambient temperature. Polymer disks were fabricated, processed, and extracted using the conditions described in Examples 1-3. The samples were all transparent and exhibited low levels of surface tackiness. For each example, multiple disks were prepared. The refractive index, Abbe number, and water content were determined on the dried disks. The average refractive indexes, Abbe numbers, and water contents are listed in Table 4. Standard deviations are reported within the parentheses.

TABLE 3

| Formulations | | | |
|---|---|---|---|
| Components (weight %) | Ex. 4 | Ex. 5 | Ex. 6 |
| EGDCA | 80.1 | 85 | 90 |
| TCDA | 2 | 4 | 1.5 |
| NHA | 16.97 | 10.07 | 7.57 |
| UVB | 0.7 | 0.7 | 0.7 |
| Omnirad 819 | 0.23 | 0.23 | 0.23 |

TABLE 4

| Physical Properties | | |
|---|---|---|
| | Average Refractive Index | Average Abbe Number | Average Water Content (weight percent) |
|---|---|---|---|
| Ex. 4 | 1.521083 (0.000055) | 50.95 (0.10) | 0.59% (0.001005) |
| Ex. 5 | 1.526440 (0.000183) | 50.81 (0.50) | 0.48% (0.001382) |
| Ex. 6 | 1.527891 (0.000129) | 50.84 (0.60) | 0.41% (0.000256) |

Examples 4-6 exhibited both high refractive index (greater than 1.50) and high Abbe number (greater than 50) making these materials suitable for ophthalmic devices such as intraocular lenses. Examples 4-6 also exhibited low water content which can provide dimensional stability for implantable ophthalmic devices.

Examples 7-10

Under yellow lighting, RMMs listed in Table 5 were degassed using vacuum for at least 7 minutes, back filling the head-space with nitrogen gas, and then immediately transferred into a fill box having a nitrogen gas atmosphere with 0.1% to 0.5% (v/v) oxygen gas and an internal temperature at ambient temperature. Polymer disks were fabricated and processed, excluding the 2-propanol extraction process, using the conditions described in Examples 1-3. The samples were all transparent and exhibited low levels of surface tackiness. For each example, multiple disks were prepared. The refractive index, Abbe number, and water content were determined on the dried disks. The average refractive indexes, Abbe numbers, and water contents are listed in Table 6. Standard deviations are reported within the parentheses.

TABLE 5

| Formulations | | | | |
|---|---|---|---|---|
| Components (weight %) | Ex. 7 | Ex. 8 | Ex. 9 | Ex. 10 |
| EGDCA | 80.1 | 85 | 90 | 92 |
| TCDA | 2 | 2 | 1.5 | 1 |
| PEG—OH 360 | 9.86 | 2.11 | 1.96 | 0.96 |
| NRA | 7.11 | 9.96 | 5.61 | 5.11 |
| UVB | 0.7 | 0.7 | 0.7 | 0.7 |
| Omnirad 819 | 0.23 | 0.23 | 0.23 | 0.23 |

TABLE 6

Physical Properties

|  | Average Refractive Index | Average Abbe Number | Average Water Content (weight percent) |
|---|---|---|---|
| Ex. 7 | 1.520733 (0.000119) | 53.11 (0.64) | 2.63% (0.001450) |
| Ex. 8 | 1.524025 (0.000055) | 51.34 (0.19) | 0.42% (0.001014) |
| Ex. 9 | 1.527039 (0.000066) | 50.89 (0.11) | 0.45% (0.001146) |
| Ex. 10 | 1.528039 (0.000102) | 50.63 (0.02) | 0.20% (0.000151) |

Examples 7-10 exhibited both high refractive index (greater than 1.50) and high Abbe number (greater than 50) making these materials suitable for ophthalmic devices such as intraocular lenses. Examples 7-10 also exhibited low water content which can provide dimensional stability for implantable ophthalmic devices.

Examples 11-13

Under yellow lighting, RMMs listed in Table 7 were degassed using vacuum for at least 7 minutes, back filling the head-space with nitrogen gas, and then immediately transferred into a fill box having a nitrogen gas atmosphere with 0.1% to 0.5% (v/v) oxygen gas and an internal temperature at ambient temperature. Polymer disks were fabricated and processed, excluding the 2-propanol extraction process, using the conditions described in Examples 1-3. The samples were all transparent and exhibited low levels of surface tackiness. For each example, multiple disks were prepared. The refractive index, Abbe number, and water content were determined on the dried disks. The average refractive indexes, Abbe numbers, and water contents are listed in Table 8. Standard deviations are reported within the parentheses.

TABLE 7

Formulations

| Components (weight %) | Ex. 11 | Ex. 12 | Ex. 13 |
|---|---|---|---|
| EGDCA | 80.1 | 90.1 | 90.1 |
| TCDA | 2 | 1 | 1 |
| PEG—OH 360 | 9.96 | 5.96 | 5.96 |
| PPA | 0 | 2.01 | 0 |
| CHPA | 7.01 | 0 | 2.01 |
| UVB | 0.7 | 0.7 | 0.7 |
| Omnirad 819 | 0.23 | 0.23 | 0.23 |

TABLE 8

Physical Properties

|  | Average Refractive Index | Average Abbe Number | Average Water Content (weight percent) |
|---|---|---|---|
| Ex. 11 | 1.523527 (0.000112) | 53.37 (0.64) | 2.72% (0.000681) |
| Ex. 12 | 1.528724 (0.000223) | 51.84 (0.31) | 1.57% (0.000304) |
| Ex. 13 | 1.527790 (0.000216) | 52.36 (0.21) | 1.41% (0.000583) |

Examples 11-13 exhibited both high refractive index (greater than 1.50) and high Abbe number (greater than 50) making these materials suitable for ophthalmic devices such as intraocular lenses. Examples 11-13 also exhibited low water content which can provide dimensional stability for implantable ophthalmic devices.

Examples 14-15

Under yellow lighting, RMMs listed in Table 9 were degassed using vacuum for at least 7 minutes, back filling the head-space with nitrogen gas, and then immediately transferred into a fill box having a nitrogen gas atmosphere with less than 0.1% to 0.5% (v/v) oxygen gas and an internal temperature at ambient temperature. Polymer disks (about 0.75 millimeters in thickness and 12-14 millimeters in diameter) were fabricated using circular plastic molds made of polypropylene. About 250 microliters of RMM were dispensed into the mold assembly, and the assembly transferred into a cure box held at a temperature between 60° C. and 65° C. and then cured from the top and bottom for a total of ninety minutes using 435 nm LED lights on both sides with the following intensity profile: 20 minutes at 5 mW/cm$^2$ (2.5 mW/cm$^2$ top and 2.5 mW/cm$^2$ bottom), 20 minutes at 10 mW/cm$^2$ (5 mW/cm$^2$ top and 5 mW/cm$^2$ bottom), 20 minutes at 20 mW/cm$^2$ (10 mW/cm$^2$ top and 10 mW/cm$^2$ bottom) and 30 minutes at 30 mW/cm$^2$ (15 mW/cm$^2$ top and 15 mW/cm$^2$ bottom). The cured assemblies were manually demolded. The samples were all transparent and exhibited low levels of surface tackiness. The disks were extracted and dried following the steps described in Examples 1-3. For each example, multiple disks were prepared. The refractive index, Abbe number, and water content were determined on the dried disks. The average refractive indexes, Abbe numbers, and water contents are listed in Table 10. Standard deviations are reported within the parentheses.

TABLE 9

Formulations

| Components (weight %) | Ex. 14 | Ex. 15 |
|---|---|---|
| EGDCA | 80.1 | 80.1 |
| TCDA | 2 | 2 |
| PEG—OH 360 | 11.06 | 11.06 |
| NHA | 4.61 | 0 |
| PPA | 0 | 4.61 |
| HEVB | 2.00 | 2.00 |
| Omnirad 819 | 0.23 | 0.23 |

TABLE 10

Physical Properties

|  | Average Refractive Index | Average Abbe Number | Average Water Content (weight percent) |
|---|---|---|---|
| Ex. 14 | 1.527358 (0.000168) | 50.68 (0.17) | 1.48% (0.00) |
| Ex. 15 | 1.532008 (.000079) | 49.56 (0.29) | 1.50% (0.00) |

Examples 14 exhibited both high refractive index (greater than 1.50) and high Abbe number (greater than 50) making this material suitable for ophthalmic devices such as intraocular lenses. Examples 14 and 15 also exhibited low water content which can provide dimensional stability for implantable ophthalmic devices. Example 15 also exhibited high refractive index (greater than 1.50), but its Abbe number was just under 50. Example 15 is still a suitable material for ophthalmic devices. Example 15 contained 6.6 weight percent aromatic monomers which lowered the Abbe number. By decreasing the amount of these aromatic monomers, the Abbe number would increase accordingly. At some reduced level of aromatic monomers, the Abbe number would be over 50.

Examples 16-21 (Prophetic)

Under yellow lighting, RMMs listed in Table 11 are degassed using vacuum for at least 7 minutes, back filling the head-space with nitrogen gas, and then immediately is transferred into a fill box having a nitrogen gas atmosphere with 0.1% to 0.5% (v/v) oxygen gas and an internal temperature at ambient temperature. Polymer disks (about 0.75 millimeters in thickness and 12-14 millimeters in diameter) are fabricated using circular plastic molds made of polypropylene. About 250 microliters of RMM are dispensed into the mold assembly, and the assembly is transferred into a cure box held at a temperature between 60° C. and 65° C. and then is cured using TL03 lights having an intensity of 6-7 mW/cm$^2$ for 90 minutes. The cured assemblies are manually demolded. The polymer disks are all transparent and exhibited low levels of surface tackiness. Each disk is extracted with 2-propanol and subsequently dried using the following steps: (a) one disk is transferred into a glass jar with 20 mL solvent and shaken at 115 rpm for 24 hours at 50° C. using an incubator/shaker, (b) the solvent is completely decanted, replaced with fresh 20 mL aliquot of 2-propanol, and shaken at 115 rpm for 1.5 hours at 50° C., (c) step (b) is repeated two more times, (d) after the final solvent decant, the polymer disk is allowed to air dry at room temperature overnight, and then (e) the disk is placed in a vacuum oven at 60-65° C. for seven days (less than one inch of Hg). For each example, the refractive index, Abbe number, and water content are determined on the dried disks.

TABLE 11

| Components (weight %) | Ex. 16 | Ex. 17 | Ex. 18 | Ex. 19 | Ex. 20 | Ex. 21 |
|---|---|---|---|---|---|---|
| Formulations | | | | | | |
| EGDCA | 85 | 80.1 | 92 | 85 | 80.1 | 92 |
| TCDA | 2 | 4 | 1 | 2 | 4 | 1 |
| PEG-OH 360 | 12.07 | 14.97 | 6.07 | 0 | 0 | 0 |
| NRA | 0 | 0 | 0 | 12.07 | 14.97 | 6.07 |
| UVB | 0.7 | 0.7 | 0.7 | 0.7 | 0.7 | 0.7 |
| Omnirad 819 | 0.23 | 0.23 | 0.23 | 0.23 | 0.23 | 0.23 |

Examples 16-21 are expected to exhibit both high refractive indexes and Abbe numbers as well as low water contents, making them suitable materials for ophthalmic devices, in particular, intraocular lenses.

Examples 22-28 (Prophetic)

Under yellow lighting, RMMs listed in Table 12 are degassed using vacuum for at least 7 minutes, back filling the head-space with nitrogen gas, and then immediately is transferred into a fill box having a nitrogen gas atmosphere with 0.1% to 0.5% (v/v) oxygen gas and an internal temperature at ambient temperature. Polymer disks are fabricated and processed, excluding the 2-propanol extraction process, using the conditions described in Examples 16-21. The samples are all transparent and exhibited low levels of surface tackiness. For each example, the refractive index, Abbe number, and water content are determined on the dried disks.

TABLE 12

| Components (weight %) | Ex. 22 | Ex. 23 | Ex. 24 | Ex. 25 | Ex. 26 | Ex. 27 | Ex. 28 |
|---|---|---|---|---|---|---|---|
| EGDCA | 80.1 | 80.1 | 85 | 92 | 80.1 | 84.1 | 84.1 |
| TCDA | 2 | 4 | 4 | 1 | 2 | 2 | 2 |
| PEG-OH 360 | 7.11 | 9.86 | 4.96 | 5.11 | 9.96 | 9.96 | 7.96 |
| NHA | 8.6 | 5.11 | 5.11 | 0.96 | 0 | 0 | 1 |
| PPA | 0 | 0 | 0 | 0 | 7.01 | 3.01 | 4.01 |
| UVB | 0.7 | 0.7 | 0.7 | 0.7 | 0.7 | 0.7 | 0.7 |
| Omnirad 819 | 0.23 | 0.23 | 0.23 | 0.23 | 0.23 | 0.23 | 0.23 |

Examples 22-28 are expected to exhibit both high refractive indexes and Abbe numbers as well as low water contents, making them suitable materials for ophthalmic devices, in particular, intraocular lenses. Examples 26-28 are expected to exhibit lower Abbe numbers than the other Examples 22-25 because of their aromatic monomer content.

Clauses

For reasons of completeness, various aspects of the disclosure are set forth in the following numbered clauses.

Clause 1. A composition made by free radical polymerization of a reactive monomer mixture comprising:
  a) at least one low glass transition temperature monomer;
  b) a tricyclo[5.2.1.0$^{2,6}$]decanedimethanol di(meth)acrylate cross-linking agent; and
  c) an ethylene glycol dicyclopentenyl ether (meth)acrylate;
wherein the concentration of the ethylene glycol dicyclopentenyl ether (meth)acrylate in the reactive monomer mixture excluding any diluent is greater than 80 weight percent; and wherein the composition exhibits a refractive index of at least 1.45 and an Abbe number of at least 39.

Clause 2. The composition of clause 1, wherein the concentration of the low glass transition temperature monomer in the reactive monomer mixture excluding any diluent is between about 1 and about 19 weight percent, between about 4 and about 17 weight percent, between about 6 and about 15 weight percent, or between about 8 and about 15 weight percent.

Clause 3. The composition of any of clauses 1-2, wherein the low glass transition temperature monomer is a hydrophilic monomer.

Clause 4. The composition of clause 4, wherein the hydrophilic monomer is a poly(ethylene glycol)-containing monomer selected from poly(ethylene glycol) (meth)acrylate, poly(ethylene glycol) methyl ether (meth)acrylate, and combinations thereof.

Clause 5. The composition of clause 4, where the hydrophilic monomer is poly(ethylene glycol) methacrylate.

Clause 6. The composition of clause 5, wherein the low glass transition temperature monomer is a hydrophobic monomer.

Clause 7. The composition of clause 6, wherein the hydrophobic monomer is a (meth)acrylate monomer selected from an aliphatic (meth)acrylate, a haloalkyl (meth)acrylate, a cycloaliphatic (meth)acrylate, an aromatic (meth)acrylate, and any combination thereof.

Clause 8. The composition of clause 7, wherein the hydrophobic monomer is an aliphatic (meth)acrylate selected from $C_1$-$C_{20}$ alkyl (meth)acrylates.

Clause 9. The composition of clause 8, wherein the aliphatic (meth)acrylate is selected from ethyl acrylate, n-propyl acrylate, n-butyl acrylate, iso-butyl acrylate, n-hexyl (meth)acrylate, 2-ethylhexyl (meth)acrylate, n-octyl (meth)acrylate, n-decyl (meth)acrylate, iso-decyl (meth) acrylate and any combination thereof.

Clause 10. The composition of clause 9, wherein the aliphatic (meth)acrylate is n-hexyl acrylate.

Clause 11. The composition of clause 7, wherein the hydrophobic monomer is a cycloaliphatic (meth)acrylate selected from 2-cyclohexylethyl acrylate, 3-cyclohexylpropyl acrylate, cyclohexylbutyl acrylate, and any combination thereof.

Clause 12. The composition of clause 11, wherein the cycloaliphatic (meth)acrylate is 3-cyclohexylpropyl acrylate.

Clause 13. The composition of clause 7, wherein the hydrophobic monomer is an aromatic (meth)acrylate selected from the group consisting of 2-phenylethyl acrylate, 3-phenylpropyl acrylate, 4-phenylbutyl acrylate, 2-phenoxyethyl acrylate, 3-phenoxypropyl acrylate, 4-phenoxybutyl acrylate, and any combination thereof.

Clause 14. The composition of clause 13, wherein the aromatic (meth)acrylate is 3-phenylpropyl acrylate.

Clause 15. The composition of any one of clauses 1-14, wherein the low glass transition temperature monomer is a monomer whose homopolymer exhibits a glass transition temperature lower than 0° C., lower than minus 5° C. (−5° C.), lower than minus 10° C. (−10° C.), lower than minus 15° C. (−15° C.), or lower than minus 20° C. (−20° C.).

Clause 16. The composition of any one of clauses 1-15, wherein the tricyclo[5.2.1.0$^{2,6}$]decanedimethanol di(meth) acrylate cross-linking agent is tricyclo[5.2.1.0$^{2,6}$]decanedimethanol diacrylate.

Clause 17. The composition of clause 16, wherein the reactive monomer mixture comprises the tricyclo[5.2.1.0$^{2,6}$]decanedimethanol diacrylate in an amount between about 0.5 weight percent and about 10 weight percent, about 0.5 weight percent and about 5 weight percent, or about 1 weight percent and about 4 weight percent.

Clause 18. The composition of any one of clauses 1-17, wherein the ethylene glycol dicyclopentenyl ether (meth) acrylate is ethylene glycol dicyclopentenyl ether acrylate.

Clause 19. The composition of clause 18, wherein the reactive monomer mixture comprises the ethylene glycol dicyclopentenyl ether acrylate in an amount between about 80.1 weight percent and about 95 weight percent, between about 80.1 weight percent and about 92 weight percent, or between about 80.1 weight percent and about 90 weight percent.

Clause 20. The composition of any one of clauses 1-19, wherein the reactive monomer mixture further comprises a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis (meth)acrylamide, poly(ethylene glycol) di(meth)acrylate, bis(2-hydropropyl (meth)acrylate) terminated polydimethylsiloxanes, and any combination thereof.

Clause 21. The composition of any one of clauses 1-20, wherein the reactive monomer mixture further comprises at least one hydroxyalkyl (meth)acrylate monomer selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof.

Clause 22. The composition of clause 21, wherein the hydroxyalkyl (meth)acrylate monomer is 2-hydroxyethyl acrylate.

Clause 23. The composition of any one of clauses 1-22, wherein the reactive monomer mixture further comprises at least one alkoxyalkyl (meth)acrylate.

Clause 24. The composition of clause 23, wherein the alkoxyalkyl (meth)acrylate comprises a linear, branched, or cyclic alkoxyalkyl group having between 1 and 25 carbon atoms and at least one oxygen atom.

Clause 25. The composition of any of clauses 1-24, wherein the reactive monomer mixture further comprises a polymer derived from an amide-containing monomer.

Clause 26. The composition of clause 25, wherein the polymer derived from an amide-containing monomer is selected from poly(vinyl pyrrolidone), poly(N-vinyl-N-methyl acetamide), poly(N-vinyl acetamide), poly(dimethyl acrylamide), and a copolymer or a mixture thereof.

Clause 27. The composition of clause 26, wherein the polymer derived from an amide-containing monomer is poly(vinyl pyrrolidone).

Clause 28. The composition of clause 25, wherein the polymer derived from an amide-containing monomer is a copolymer.

Clause 29. The composition of any one of clauses 25-28, wherein the reactive monomer mixture comprises the polymer derived from an amide-containing monomer in an amount between about 0.1 weight percent and about 5 weight percent, between about 0.5 weight percent and about 3 weight percent, or between about 0.5 weight percent and about 2 weight percent.

Clause 30. The composition of any one of clauses 1-29, wherein the reactive monomer mixture further comprises at least one hydroxy silicone monomer.

Clause 31. The composition of clause 30, wherein the hydroxy silicone monomer comprises mono-n-butyl terminated mono-(2-hydroxy-3-methacryloxypropyloxy)-propyl terminated polydimethylsiloxane, 3-(3-(1,1,1,3,5,5,5-heptamethyltrisiloxan-3-yl)propoxy)-2-hydroxypropyl methacrylate, 3-(3-(1,5-di-tert-butyl-1,1,3,5,5-pentamethyltrisiloxan-3-yl)propoxy)-2-hydroxypropyl methacrylate, or any combination thereof.

Clause 32. The composition of clause 30 or clause 31, wherein the reactive monomer mixture comprises the hydroxy silicone monomer in an amount between about 1 and about 25 weight percent, between about 5 and about 20 weight percent, or between about 10 and about 20 weight percent.

Clause 33. The composition of any one of clauses 1-32, wherein the reactive monomer mixture further comprises a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis (meth)acrylamide, poly(ethylene glycol) di(meth)acrylate, bis(2-hydropropyl (meth)acrylate) terminated polydimethylsiloxanes, and any combination thereof.

Clause 34. The composition of any one of clauses 1-33, wherein the reactive monomer mixture further comprises at least one UV/HEV absorbing compound.

Clause 35. The composition of clause 34, wherein the UV/HEV absorbing compound is a compound of Formula I, 2-(2'-hydroxy-5-methacrylyloxyethylphenyl)-2H-benzotriazole, 2-(2-cyano-2-(9H-thioxanthen-9-ylidene)acetamido) ethyl methacrylate, 2-(2-cyano-2-(9H-xanthen-9-ylidene) acetamido)ethyl methacrylate, 2-(2-cyano-2-(10- methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof.

Clause 36. The composition of any one of clauses 1-35, wherein the reactive monomer mixture further comprises at least one diluent.

Clause 37. The composition of any one of clauses 1-36, having a water content of between about 0 weight percent and about 15 weight percent, about 1 weight percent and about 10 weight percent, or about 1 weight percent and about 5 weight percent.

Clause 38. The composition of any one of clauses 1-37, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 39. The composition of any one of clauses 1-38, wherein the free radical polymerization is a photopolymerization using a bisacylphosphine oxide initiator.

Clause 40. An ophthalmic device comprising the composition of any one of clauses 1-39.

Clause 41. The ophthalmic device of clause 40 wherein the ophthalmic device comprises an intraocular lens, contact lens, corneal inlay, corneal outlay, or corneal insert.

Clause 42. A method for making an ophthalmic device, the method comprising:
providing a composition of any one of clauses 1-39; and forming an ophthalmic device.

Clause 43. The method of clause 42, further comprising the step of extracting the ophthalmic device with a solvent.

Clause 44. The method of clause 43, further comprising the step of hydrating the extracted ophthalmic device with at least one aqueous solution.

Clause 45. A method for making an ophthalmic device, the method comprising:
preparing a blank from the composition any of clauses 1-39; and
machining an ophthalmic device from the blank.

Clause 46. The method of clause 45, further comprising the step of extracting the ophthalmic device with a solvent.

Clause 47. The method of clause 46, further comprising the step of hydrating the extracted ophthalmic device with at least one aqueous solution.

Clause 48. The method of any one of clauses 42-47, further comprising an irradiation step using a femtosecond two photon laser.

Clause 49. The method of any of clauses 42-48, further comprising a step of sterilizing the ophthalmic device.

Clause 50. A method for making an ophthalmic device, the method comprising molding the device from the composition any of clauses 1-39.

We claim:
1. A composition made by free radical polymerization of a reactive monomer mixture comprising:
 a) at least one low glass transition temperature monomer;
 b) a tricyclo[5.2.1.0$^{2,6}$]decanedimethanol di(meth)acrylate cross-linking agent; and
 c) an ethylene glycol dicyclopentenyl ether (meth)acrylate;
wherein the concentration of the ethylene glycol dicyclopentenyl ether (meth)acrylate in the reactive monomer mixture excluding any diluent is greater than 80 weight percent; and
wherein the composition exhibits a refractive index of at least 1.45 and an Abbe number of at least 39.

2. The composition of claim 1, wherein the reactive monomer mixture comprises the at least one low glass transition temperature monomer in an amount between about 1 and about 19 weight percent, between about 4 and about 17 weight percent, between about 6 and about 15 weight percent, or between about 8 and about 15 weight percent.

3. The composition of claim 1, wherein the at least one low glass transition temperature monomer is a hydrophilic monomer.

4. The composition of claim 3, wherein the hydrophilic monomer is a poly(ethylene glycol)-containing monomer selected from poly(ethylene glycol) (meth)acrylate, poly(ethylene glycol) methyl ether (meth)acrylate, and combinations thereof.

5. The composition of claim 1, wherein the at least one low glass transition temperature monomer is a hydrophobic monomer.

6. The composition of claim 5, wherein the hydrophobic monomer is a (meth)acrylate monomer selected from an aliphatic (meth)acrylate, a haloalkyl (meth)acrylate, a cycloaliphatic (meth)acrylate, an aromatic (meth)acrylate, and any combination thereof.

7. The composition of claim 6, wherein the aliphatic (meth)acrylate is selected from ethyl acrylate, n-propyl acrylate, n-butyl acrylate, iso-butyl acrylate, n-hexyl (meth)acrylate, 2-ethylhexyl (meth)acrylate, n-octyl (meth)acrylate, n-decyl (meth)acrylate, iso-decyl (meth)acrylate, and any combination thereof.

8. The composition of claim 6, wherein the hydrophobic monomer is a cycloaliphatic (meth)acrylate selected from 2-cyclohexylethyl acrylate, 3-cyclohexylpropyl acrylate, 4-cyclohexylbutyl acrylate, and any combination thereof.

9. The composition of claim 6, wherein the hydrophobic monomer is an aromatic (meth)acrylate selected from the group consisting of 2-phenylethyl acrylate, 3-phenylpropyl acrylate, 4-phenylbutyl acrylate, 2-phenoxyethyl acrylate, 3-phenoxypropyl acrylate, 4-phenoxybutyl acrylate, and any combination thereof.

10. The composition of claim 5, wherein the hydrophobic monomer is a hydroxy silicone monomer selected from 3-(3-(1,1,1,3,5,5,5-heptamethyltrisiloxan-3-yl)propoxy)-2-hydroxypropyl methacrylate, mono-n-butyl terminated monomethacryloxypropyl terminated polydimethylsiloxane, and mono-(2-hydroxy-3-methacryloxypropyl)-propyl ether terminated mono-n-butyl terminated polydimethylsiloxane, and any combination thereof.

11. The composition of claim 1, wherein the at least one low glass transition temperature monomer is a monomer whose homopolymer exhibits a glass transition temperature lower than 0° C., lower than minus 5° C. (−5° C.), lower than minus 10° C. (−10° C.), lower than minus 15° C. (−15° C.), or lower than minus 20° C. (−20° C.).

12. The composition of claim 1, wherein the tricyclo[5.2.1.0$^{2,6}$]decanedimethanol di(meth)acrylate cross-linking agent is tricyclo[5.2.1.0$^{2,6}$]decanedimethanol diacrylate.

13. The composition of claim 12, wherein the reactive monomer mixture comprises the tricyclo[5.2.1.0$^{2,6}$]decanedimethanol diacrylate in an amount between about 0.5 weight percent and about 10 weight percent, about 0.5 weight percent and about 5 weight percent, or about 1 weight percent and about 4 weight percent.

14. The composition of any one of claim 1, wherein the ethylene glycol dicyclopentenyl ether (meth)acrylate is ethylene glycol dicyclopentenyl ether acrylate.

15. The composition of claim 14, wherein the reactive monomer mixture comprises the ethylene glycol dicyclopentenyl ether acrylate in an amount between about 80.1 weight percent and about 95 weight percent, between about 80.1 weight percent and about 92 weight percent, or between about 80.1 weight percent and about 90 weight percent.

16. The composition of claim 1, wherein the reactive monomer mixture further comprises a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis(meth)acrylamide, poly(ethylene glycol) di(meth)acrylate, bis(2-hydropropyl (meth)acrylate) terminated polydimethylsiloxanes, and any combination thereof.

17. The composition of claim 1, wherein the reactive monomer mixture further comprises at least one hydroxyalkyl (meth)acrylate monomer selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof.

18. The composition of claim 1, wherein the reactive monomer mixture further comprises at least one UV/HEV absorbing compound.

19. The composition of claim 1, wherein the reactive monomer mixture further comprises at least one hydroxy silicone monomer.

20. The composition of claim 19, wherein the at least one hydroxy silicone monomer comprises mono-n-butyl terminated mono-(2-hydroxy-3-methacryloxypropyloxy)-propyl terminated polydimethylsiloxane, 3-(3-(1,1,1,3,5,5,5-heptamethyltrisiloxan-3-yl)propoxy)-2-hydroxypropyl methacrylate, 3-(3-(1,5-di-tert-butyl-1,1,3,5,5-pentamethyltrisiloxan-3-yl)propoxy)-2-hydroxypropyl methacrylate, or any combination thereof.

21. The composition of claim 19, wherein the reactive monomer mixture comprises the at least one hydroxy silicone monomer in an amount between about 1 and about 25 weight percent.

22. The composition of claim 1, having a water content of between about 0 weight percent and about 15 weight percent, about 1 weight percent and about 10 weight percent, or about 1 weight percent and about 5 weight percent.

23. The composition of claim 1, wherein the composition has a refractive index of at least 1.45 and an Abbe number of at least 45.

24. An ophthalmic device comprising the composition of claim 1, wherein the ophthalmic device comprises an intraocular lens, contact lens, corneal inlay, corneal onlay or corneal insert.

25. A method for making an ophthalmic device, the method comprising:
   a. providing a composition of any claim 1; and
   b. forming an ophthalmic device.

* * * * *